US012611477B2

(12) United States Patent
Kobe et al.

(10) Patent No.: US 12,611,477 B2
(45) Date of Patent: *Apr. 28, 2026

(54) ETHYLENE OXIDE STERILIZATION SENSOR INCLUDING THERMAL INDICATOR COMPONENT AND ACID-FUNCTIONAL SORBENT OR NONWOVEN FIBROUS SUBSTRATE, AND METHOD OF USE

(71) Applicant: 3M INNOVATIVE PROPERTIES COMPANY, St. Paul, MN (US)

(72) Inventors: Michael W. Kobe, Lake Elmo, MN (US); Michael S. Wendland, North St. Paul, MN (US); Richard C. Webb, St. Paul, MN (US); Michael E. Hamerly, Vadnais Heights, MN (US); Daniel J. O'Neal, St. Paul, MN (US); Kelvin J. Witcher, Hudson, WI (US); Dawud H. Tan, Lakeland, MN (US); Daniel J. Zillig, Woodbury, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 1065 days.

This patent is subject to a terminal disclaimer.

(21) Appl. No.: 17/708,475

(22) Filed: Mar. 30, 2022

(65) Prior Publication Data

US 2022/0387653 A1 Dec. 8, 2022

Related U.S. Application Data

(60) Provisional application No. 63/192,736, filed on May 25, 2021.

(51) Int. Cl.
*A61L 2/28* (2006.01)
*A61L 2/206* (2026.01)
(Continued)

(52) U.S. Cl.
CPC ................. *A61L 2/28* (2013.01); *A61L 2/206* (2013.01); *B01J 20/261* (2013.01); *C08J 5/18* (2013.01);
(Continued)

(58) Field of Classification Search
CPC ........ A61L 2/28; A61L 2/206; A61L 2202/14; B01J 20/261; B01J 2220/445; C08J 5/18;
(Continued)

(56) References Cited

U.S. PATENT DOCUMENTS

| | | | |
|---|---|---|---|
| 3,531,463 A | 9/1970 | Gustafson | |
| 3,825,380 A | 7/1974 | Harding | |
| (Continued) | | | |

FOREIGN PATENT DOCUMENTS

| | | |
|---|---|---|
| EP | 0818676 | 1/1998 |
| JP | H03-125950 | 5/1991 |
| (Continued) | | |

OTHER PUBLICATIONS

Ahn, "Rapid Generation and Control of Microporosity, Bimodal Pore Size Distribution, and Surface Area in Davankov-Type Hyper-Cross-Linked Resins", Macromolecules, 2006, vol. 39, pp. 627-632.
(Continued)

*Primary Examiner* — Elizabeth A Robinson
*Assistant Examiner* — Sophia Y Lyle
(74) *Attorney, Agent, or Firm* — Adrian L. Pishko

(57) ABSTRACT

The present disclosure provides an ethylene oxide sterilization sensor and method of use. The sensor includes: at least one thermal indicator component independently selected from an electronic thermal sensor, an irreversible temperature indicator, and a heat-shrinkable film; an acid-functional porous sorbent or an acid-functional nonwoven fibrous substrate in thermal contact with the at least one thermal indicator component; and an acid having a boiling point
(Continued)

above 120° C. and a pKa of no greater than 2.5. The acid is impregnated in or covalently attached to the porous sorbent or is covalently attached to the nonwoven fibrous substrate. The sensor includes at least one of the electronic thermal sensor, the irreversible temperature indicator, or the acid-functional nonwoven fibrous substrate.

19 Claims, 5 Drawing Sheets

(51) Int. Cl.

| | |
|---|---|
| *B01J 20/26* | (2006.01) |
| *C08J 5/18* | (2006.01) |
| *C08J 7/14* | (2006.01) |

(52) U.S. Cl.
CPC ............. *C08J 7/14* (2013.01); *A61L 2202/14* (2013.01); *B01J 2220/445* (2013.01); *C08J 2323/10* (2013.01)

(58) Field of Classification Search
CPC ......... C08J 7/14; C08J 2323/10; G01N 25/28; G01N 25/32; C12Q 1/22; C12M 37/06
See application file for complete search history.

(56) References Cited

U.S. PATENT DOCUMENTS

| | | | | |
|---|---|---|---|---|
| 3,981,683 | A | * | 9/1976 | Larsson ............... G01N 31/226 |
| | | | | 374/106 |
| 4,138,216 | A | | 2/1979 | Larsson |
| 4,436,858 | A | | 3/1984 | Klosiewicz |
| 4,448,548 | A | | 5/1984 | Foley |
| D315,600 | S | | 3/1991 | Niven |
| 5,145,935 | A | | 9/1992 | Hayashi |
| 5,155,199 | A | | 10/1992 | Hayashi |
| RE34,515 | E | | 1/1994 | Foley |
| 5,378,430 | A | | 1/1995 | Nieves |
| 5,451,372 | A | | 9/1995 | Larsson |
| 5,506,300 | A | | 4/1996 | Ward |
| 5,665,822 | A | | 9/1997 | Bitler |
| 5,745,039 | A | * | 4/1998 | Hof .......................... G01K 3/04 |
| | | | | 335/215 |
| 5,879,631 | A | | 3/1999 | Wewers |
| 6,160,084 | A | | 12/2000 | Langer |
| 6,388,043 | B1 | | 5/2002 | Langer |
| 6,416,487 | B1 | | 7/2002 | Braverman |
| 6,423,421 | B1 | | 7/2002 | Banaszak |
| 6,451,272 | B1 | | 9/2002 | Fryer |
| 7,173,096 | B2 | | 2/2007 | Mather |
| 7,893,179 | B2 | | 2/2011 | Anderson |
| 9,134,251 | B2 | | 9/2015 | Thomas |
| 9,563,833 | B2 | | 2/2017 | Swager |
| 2001/0036670 | A1 | * | 11/2001 | Fryer ................... G01N 31/226 |
| | | | | 422/62 |
| 2002/0151084 | A1 | * | 10/2002 | Lippold ............... G01N 31/223 |
| | | | | 436/163 |
| 2005/0244353 | A1 | | 11/2005 | Lendlein |
| 2006/0041089 | A1 | | 2/2006 | Mather |

| | | | | |
|---|---|---|---|---|
| 2007/0009465 | A1 | | 1/2007 | Lendlein |
| 2007/0282181 | A1 | | 12/2007 | Findlay |
| 2008/0273572 | A1 | | 11/2008 | Lawrence |
| 2010/0081165 | A1 | * | 4/2010 | Pasmore ................ C12M 37/06 |
| | | | | 435/31 |
| 2011/0036782 | A1 | * | 2/2011 | DiLeo ........................ A61L 2/28 |
| | | | | 210/741 |
| 2019/0024137 | A1 | * | 1/2019 | Bala ..................... G01N 31/226 |

FOREIGN PATENT DOCUMENTS

| | | | | |
|---|---|---|---|---|
| WO | WO-03037391 A1 | * | 5/2003 | ............... A61L 2/28 |
| WO | WO 2006-117328 | | 11/2006 | |
| WO | WO 2017-106434 | | 6/2017 | |
| WO | WO 2019-043580 | | 3/2019 | |
| WO | WO 2021-154347 | | 5/2021 | |

OTHER PUBLICATIONS

Davies, "The Separation of Airborne Dust and Particles", Institute of Mechanical Engineers, Proceedings 1B, 1952, pp. 185-213.

Davankov, "Structure and properties of Hypercrosslinked polystyrene—the first representative of a new class of polymer networks", Reactive Polymers, 1990, vol. 13, pp. 27-42.

Hussein, "New Technologies for Active Disassembly: Using the Shape Memory Effect in Engineering Polymers", Int. J. Product Development, 2008, vol. 06, pp. 431-449.

Kobe, "Hydrogen Peroxide Sterilization Sensor Including Thermal Indicator Component and Reactant-Functional Sorbent, and Method of Use", U.S. Appl. No. 17/712,223, filed Apr. 4, 2022, 34 pages.

Li, "A New Strategy to Microporous Polymers: Knitting Rigid Aromatic Building Blocks by External Cross-Linker", Macromolecules, 2011, vol. 44, pp. 2410-2414.

Liu, "Unexpected Behavior of 1-Chlorodecane as a Novel Porogen in the Preparation of High-Porosity Poly(divinylbenzene) Microspheres", J. Phys. Chem. C, 2008, vol. 112, pp. 13171-13174.

Mohamed, "Porous copolymer resins: Tuning pore structure and surface area with non-reactive Porogens", Nanomaterials, 2012, vol. 2, pp. 163-186.

Wei, "Solvothermal synthesis of highly porous polymers and their controllable transition from macro/mesoporosity to meso/microporosity", Colloids and Surfaces A: Physiochemical Engineering Aspects, 2012, vol. 414, pp. 327-332.

Wendland, "Ammonia Sensor Including Thermal Indicator Component and Acid-Functional Sorbent, and Method of Use", U.S. Appl. No. 17/708,533, filed Mar. 30, 2022, 42 pages.

Wood, "Hydrogen Storage in Microporous Hypercrosslinked Organic Polymer Networks", Chem. Mater., 2007, vol. 19, pp. 2034-2048.

Yin-Lin, "Charged Depth Filter for Therapeutic Biotechnology Manufacturing Process", PCT Application No. IB2022/051648, filed Feb. 24, 2022, 49 pages.

Zhang, "Superhydrophobic nanoporous polymers as efficient adsorbents for organic compounds", Nano Today, 2009, vol. 04, pp. 135-142.

Nyhus, "Formation of the Porous Structure During the Polymerization of meta-Divinylbenzene and paraDivinylbenzene with Toluene and 2-Ethylhexanoic Acid (2-EHA) as Porogens", J. Poly. Sci. Part A: Polymer Chemistry, 1999, vol. 37, pp. 3973-3990.

Reaxys search results, Aug. 8, 2025, 31 pages.

* cited by examiner

ETHYLENE OXIDE STERILIZATION SENSOR INCLUDING THERMAL INDICATOR COMPONENT AND ACID-FUNCTIONAL SORBENT OR NONWOVEN FIBROUS SUBSTRATE, AND METHOD OF USE

BACKGROUND

Ethylene oxide (EO) is one of four typical forms of sterilization along with steam, hydrogen peroxide, and ultraviolet (UV). Ethylene oxide is used at low temperatures to sterilize temperature sensitive materials and equipment. Ethylene oxide sterilization is usually performed in a sealed chamber. Often, such chamber is packed with materials and equipment during the sterilization process. Packing the chamber to its maximum capacity to have the highest rate of turnover for materials needing to be sterilized occurs because the whole process can take quite a while, in some cases a whole day. The time-consuming step in the ethylene oxide sterilization process is the aeration of the chamber where the ethylene oxide is completely flushed out with air. Due to electrical constraints with the design of the chamber, only Venturi pumps can be used during the chamber flush, which tend to be relatively low flowing, hence the long aeration time.

With the chamber typically being filled to capacity during the sterilization process, it is not uncommon for areas in the chamber to never see full exposure to ethylene oxide resulting in some items not being properly sterilized. It is important then to have sensors scattered throughout the chamber that can be analyzed to ensure that proper and complete sterilization occurred everywhere. These sensors can be indicators, which indicate that one process condition has been met, or integrators, which indicate two or more process conditions have been met.

Process conditions include ethylene oxide concentration, time, relative humidity (RH), and pressure. The most reliable method of sterilization indication is using biological indicators. In this method, tubes containing spores are placed in various locations throughout the chamber. Upon completion of the sterilization cycle, the tubes are collected from the chamber and analyzed to ensure that the spores have been killed. It can be common for dozens of tubes to be used for each cycle. Analysis of each tube takes at least 24 minutes to complete, so it can take hours after a cycle is complete to ensure proper sterilization occurred. The biological indicators are also more expensive compared to other indicators.

SUMMARY

In a first aspect, the present disclosure provides an ethylene oxide sterilization sensor. The sensor comprises: at least one thermal indicator component independently selected from an electronic thermal sensor, an irreversible temperature indicator, or a heat-shrinkable film; an acid-functional porous sorbent or an acid-functional nonwoven fibrous substrate in thermal contact (which may or may not be direct physical contact) with the at least one thermal indicator component; and an acid having a boiling point above 120° C. and a pKa of no greater than 2.5, wherein the acid is impregnated in or covalently attached to the porous sorbent or is covalently attached to the nonwoven fibrous substrate. The sensor comprises at least one of the electronic thermal sensor, the irreversible temperature indicator, or the acid-functional nonwoven fibrous substrate.

In a second aspect, the present disclosure provides an array comprising a plurality of the ethylene oxide sterilization sensors according to the first aspect.

In a third aspect, the present disclosure provides a method of detecting ethylene oxide in a sterilization process. The method comprises: providing an ethylene oxide sterilization sensor according to the first aspect; allowing ethylene oxide to contact the acid in contact with the porous sorbent to generate thermal energy sufficient to cause a response from the at least one thermal indicator component; and detecting that conditions for ethylene oxide sterilization have been met (e.g., ethylene oxide concentration).

This sensor utilizes an exothermic interaction between ethylene oxide and the acid in contact with the (high surface area) porous sorbent or nonwoven fibrous substrate. The heat generated from the interaction, which can be both catalytic and reactive, causes a detectable response from the thermal indicator component(s), for instance a dimensional change in a heat-shrinkable film and/or an electronic signal (or end to an electronic signal) in an electronic thermal sensor. The detectable response from the thermal indicator component(s), as a result of this activation by ethylene oxide, is what indicates that conditions for ethylene oxide sterilization have been met (e.g., proper sterilization).

The above summary of the present disclosure is not intended to describe each disclosed embodiment or every implementation of the present disclosure. The description that follows more particularly exemplifies illustrative embodiments. In several places throughout the application, guidance is provided through lists of examples, which examples may be used in various combinations. In each instance, the recited list serves only as a representative group and should not be interpreted as an exclusive list.

BRIEF DESCRIPTION OF THE DRAWINGS

FIG. 1c is a schematic top view of the EO sterilization sensor of FIG. 1a after activation by EO.

Figure 1A:
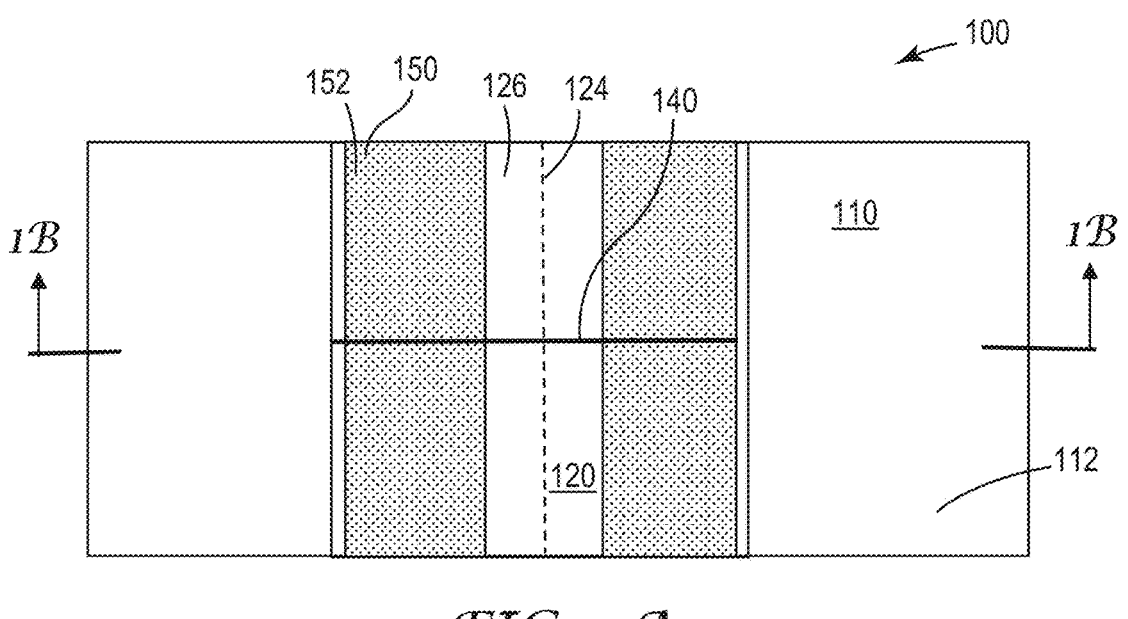
FIG. 1a is a schematic top view of an exemplary ethylene oxide (EO) sterilization sensor according to the present disclosure, before activation by EO

While the above-identified figures set forth several embodiments of the disclosure, other embodiments are also contemplated, as noted in the description. The figures are not necessarily drawn to scale. In all cases, this disclosure presents the invention by way of representation and not limitation.

DETAILED DESCRIPTION OF ILLUSTRATIVE EMBODIMENTS

Glossary

The term "comprises" and variations thereof do not have a limiting meaning where these terms appear in the description and claims. Such terms will be understood to imply the inclusion of a stated step or element or group of steps or elements but not the exclusion of any other step or element or group of steps or elements. By "consisting of" is meant including, and limited to, whatever follows the phrase "consisting of" Thus, the phrase "consisting of" indicates that the listed elements are required or mandatory, and that no other elements may be present.

The words "preferred" and "preferably" refer to embodiments of the disclosure that may afford certain benefits, under certain circumstances. However, other embodiments may also be preferred, under the same or other circumstances. Furthermore, the recitation of one or more preferred embodiments does not imply that other embodiments are not useful and is not intended to exclude other embodiments from the scope of the disclosure.

In this application, terms such as "a," "an," and "the" are not intended to refer to only a singular entity but include the general class of which a specific example may be used for illustration. The terms "a," "an," and "the" are used interchangeably with the phrases "at least one" and "one or more." The phrases "at least one of" and "comprises at least one of" followed by a list refers to any one of the items in the list and any combination of two or more items in the list.

The term "and/or" means one or all the listed elements or a combination of any two or more of the listed elements. The term "or" is generally employed in its usual sense including "and/or" unless the content clearly dictates otherwise.

Also, all numbers are assumed to be modified by the term "about" and in certain embodiments, preferably, by the term "exactly." As used herein in connection with a measured quantity, the term "about" refers to that variation in the measured quantity as would be expected by the skilled artisan making the measurement and exercising a level of care commensurate with the objective of the measurement and the precision of the measuring equipment used. Herein, "up to" a number (e.g., up to 50) includes the number (e.g., 50).

Reference throughout this specification to "one embodiment," "an embodiment," "certain embodiments," or "some embodiments," etc., means that a particular feature, configuration, composition, or characteristic described in connection with the embodiment is included in at least one embodiment of the disclosure. Thus, the appearances of such phrases in various places throughout this specification are not necessarily referring to the same embodiment of the disclosure. Furthermore, the particular features, configurations, compositions, or characteristics may be combined in any suitable manner in one or more embodiments.

The present disclosure provides an ethylene oxide sterilization sensor that includes one or more thermal indicator component(s) and an acid-functional sorbent or an acid-functional nonwoven fibrous substrate. In a first aspect, an ethylene oxide sterilization sensor comprises:

> at least one thermal indicator component independently selected from an electronic thermal sensor, an irreversible temperature indicator, and a heat-shrinkable film;
>
> an acid-functional porous sorbent or an acid-functional nonwoven fibrous substrate in thermal contact with the at least one thermal indicator component; and
>
> an acid having a boiling point above 120° C. and a pKa of no greater than 2.5, wherein the acid is impregnated in or covalently attached to the porous sorbent or is covalently attached to the nonwoven fibrous substrate;
>
> with the proviso that the sensor comprises at least one of the electronic thermal sensor, the irreversible temperature indicator, or the acid-functional nonwoven fibrous substrate.

In a second aspect, the present disclosure provides an array comprising a plurality of the ethylene oxide sterilization sensors according to any embodiment(s) of the first aspect. The array may include a plurality of the same sensor or any combination of different embodiments of the ethylene oxide sterilization sensors described in the first aspect above.

In a third aspect, the present disclosure also provides a method of detecting ethylene oxide in a sterilization process. The method comprises:

> providing an ethylene oxide sterilization sensor (according to any embodiment of the first aspect);
>
> allowing ethylene oxide to contact the acid to generate thermal energy sufficient to cause a response from the at least one thermal indicator component; and
>
> detecting that conditions for ethylene oxide sterilization have been met.

Optionally, the detecting comprises exposing an underlying image.

Each of the first, second, and third aspect are discussed in detail below.

In certain embodiments, the acid-functional porous sorbent or the acid-functional nonwoven fibrous substrate is adhered to the thermal indicator component, such as by using an adhesive (e.g., a layer of adhesive) or mechanical fastener (e.g., a clip or a clamp). In some embodiments, both an acid-functional porous sorbent and an acid-functional nonwoven fibrous substrate can be employed. Multiple such ethylene oxide sterilization sensors can be incorporated into an array if desired.

This sensor involves an ethylene oxide presence indicator that utilizes an exothermic interaction between ethylene oxide and the acid. The heat generated from the interaction, which can be both catalytic and reactive, causes a detectable response from the thermal indicator component(s), for instance a dimensional change (i.e., shrinkage) in a heat-shrinkable film, an electronic signal in an electronic thermal sensor, and/or a color change in an irreversible temperature indicator. The detectable response from the thermal indicator component(s), as a result of this activation by ethylene oxide, is what indicates that conditions for ethylene oxide sterilization have been met. The degree of the response will depend on the amount of heat to which the thermal indicator component is exposed, which will depend on the amount of ethylene oxide to which the acid-functional sorbent or acid-functional nonwoven fibrous substrate is exposed.

The at least one thermal indicator component is independently selected from the group consisting of an electronic thermal sensor, an irreversible temperature indicator, and a heat-shrinkable film. When an electronic thermal sensor is present it often comprises at least one of a thermocouple, a resistor, a capacitor, an inductor, or an electronic circuit that changes (e.g., the output voltage or current alters, or at least one portion of the circuit fails) when exposed to a specific minimum elevated temperature. Depending on the particular thermal indicator component, any combination of these are included in an electronic thermal sensor. In some cases, the electronic thermal sensor comprises a thermocouple, e.g., an open junction thermocouple. In various embodiments, for instance and without limitation, T-type, J-type, or E-type thermocouples, may be conveniently used. In some cases, the electronic thermal sensor comprises an electronic circuit that fails when exposed to a specific minimum elevated temperature. Often, the specific minimum elevated temperature is 40 degrees Celsius (° C.), 45° C., 50° C., 55° C. or even 60° C. The electronic circuit may comprise a plurality of electric or electronic components, like, for example, electrodes, wires, capacitors, transistors, resistors, inductors, wire coils, or integrated circuits. The electronic circuit may exhibit a detectable change to its operation as a result of exposure to the specific minimum elevated temperature. The electronic circuit may fail, for instance due to expansion and contraction of at least one component of the circuit, burning/melting of at least one circuit component, a substrate (e.g., heat-shrinkable substrate) that deforms, etc. In some cases, the electronic thermal sensor comprises a resistor. Resistors are well known in the art and their resistance changes with temperature, thus acting as temperature sensors. In some cases, the electronic thermal sensor comprises a capacitor. Capacitors are well known in the art and maintain an electric charge between conductive plates. Some capacitors that are used in sensors change their values in response to a stimulus, such as temperature, thus acting as temperature sensors. In some cases, the electronic thermal sensor comprises an inductor. Inductors are well known in the art. Some inductors that are used in sensors change their values in response to a stimulus, such as temperature, thus acting as temperature sensors.

In some cases, the electronic thermal sensor comprises an RFID (radio-frequency identification) tag. Radio-frequency identification uses electromagnetic fields to identify and track tags, such as RFID tags attached to objects. In operation, an RF reader sends out RF signals (e.g., through an antenna) to create an electromagnetic field. The field activates one or more RFID tags, which each produce a response that provides identifying information back to the RFID reader. When exposed to at least a certain minimum temperature, one or more electronic components of the RFID will fail and no longer produce a response, like an electronic circuit that fails, or a substrate (e.g., shrinkable substrate) that deforms, when exposed to a specific minimum elevated temperature. Once the RF reader ceases to receive the response from the RFID tag that has been exposed to heat, the detectable response from the thermal indicator component comprising an RFID tag is obtained. Alternatively, the RFID tag may have at least one component that provides an altered response to the RF reader in response to heat, to provide a detectable response.

When the irreversible temperature indicator is present, it often comprises a thermochromic dye. Suitable indicators having a thermochromic dye include, for instance, single use multiple-point temperature-indicating labels commercially available from McMaster-Carr (Elmhurst, IL), which can be attached to an object using the adhesive provided on the back of the label and show incremental temperature changes. Such labels operate by including a plurality of windows on the front face of the labels that (permanently) change color, such as by turning from white to black, when the temperature reaches each identified temperature point. For use herein, either an acid-functional porous sorbent or an acid-functional nonwoven fibrous substrate is placed in thermal contact with the irreversible temperature indicator, e.g., such as in contact with the adhesive on the back of a temperature-indicating label.

When the heat-shrinkable film is present, the shrinkage of the heat-shrinkable film provides a visual indicator. For example, the original dimensions of the film can simply be noted by an outline around it. Shrinkage of the film results in revealing of the outline. Alternatively, or additionally, shrinkage of the film can reveal an underlying picture, word, colored feature, or differently colored backing substrate.

The sensors of the present disclosure can be tailored by several factors in the construction of the sensor. Such factors include, for example, the sorbent loading in terms of grams sorbent per square meter of an area of the sensor on which the sorbent is disposed, the identity of the acid, the concentration of acid in terms of millimoles per gram or weight percent per gram of acid-functional porous sorbent or acid-functional nonwoven fibrous substrate, and the type of thermal indicator component. When the acid-functional porous sorbent or acid-functional nonwoven fibrous substrate is adhered to the thermal indicator component using a layer of an adhesive, the layer of adhesive can function as a buffer or insulator. Thus, the thickness of the adhesive can be tailored to control the extent of thermal response from the thermal indicator component.

In certain embodiments, a plurality of ethylene oxide sensors of the present disclosure may be included in an array. In such an array, each of the ethylene oxide sensors may respond differently to ethylene oxide. The sensors in the array may vary with respect to the concentration of acid in the sorbent and/or nonwoven fibrous substrate, the identity of the acid, type of thermal indicator component, and/or the thickness of an (optional) adhesive. Using this variability between sensors of an array can be utilized, for example, to indicate different levels of ethylene oxide.

The heat generated from the interaction of ethylene oxide and the acid, which can be both catalytic and reactive, causes a detectable response from the thermal indicator component(s), for instance a dimensional change (i.e., shrinkage) in a heat-shrinkable film, an electronic signal in an electronic thermal sensor, and/or a color change in an irreversible temperature indicator. The detectable response from the thermal indicator component(s), as a result of this activation by ethylene oxide, is what indicates that conditions for ethylene oxide sterilization have been met. The degree of the response will depend on the amount of heat generated, which is dependent on the amount of ethylene oxide to which the acid-functional porous sorbent or an acid-functional nonwoven fibrous substrate was exposed.

Typically, sufficient thermal energy is generated to indicate that conditions for ethylene oxide sterilization have been met at a concentration and/or exposure time that is above the required ethylene oxide concentration (600 mg/L+/−30 mg/L) or exposure time (3 hours at 37° C. or 1 hour at 55° C.) required for the sterilization process. In some cases, an ethylene oxide sterilization sensor detects ethylene oxide at a concentration of 3,000 parts per million (ppm) or greater in a gas (e.g., the gas(es) within a sterilization chamber), such as 5,000 ppm or greater, 7,000 ppm or greater, 10,000 ppm or greater, 25,000 ppm or greater, 50,000 ppm or greater, 75,000 ppm or greater, 100,000 ppm or greater, 150,000 ppm or greater, 200,000 ppm or greater, or 250,000 ppm or greater; and 500,000 ppm or less ethylene oxide in a gas. Other parameters of ethylene oxide steril-
ization processes include relative humidity (40-60% RH+/−
10%) at typical temperatures 37° C. and 55° C. and ambient
pressure.

In certain embodiments, the sensor indicates that condi-
tions for ethylene oxide sterilization have been met by
exposing an underlying visual indicator (e.g., image). Alter-
natively, the sensor indicates that conditions for ethylene
oxide sterilization have been met by creating a visual
indicator on the film. In certain embodiments, the sensor
indicates that conditions for ethylene oxide sterilization have
been met by producing a detectable response from an
electronic thermal sensor.

In certain embodiments, shrinkage in one dimension of a
heat-shrinkable film is at least 5%, at least 8%, or at least
10%. In certain embodiments, shrinkage in the total area of
a heat-shrinkable film is at least 10%, at least 15%, or at least
18%. In certain embodiments, shrinkage of the film results
in separating or tearing perforations in the heat-shrinkable
film.

Acid-Functional Porous Sorbent and Acid-Functional Nonwoven Fibrous Substrate A porous sorbent or nonwoven fibrous substrate in ther-
mal contact with the thermal indicator component is also in
contact with an acid. In this context, an "acid" includes acid
compounds as well as acid moieties. The porous sorbent
functions as a scaffold for one or more acids, whether such
acid is impregnated therein or covalently attached thereto.
Hence, such sorbent is referred to herein as an "acid-
functional porous sorbent" when it includes covalently
attached acid moieties or impregnated acid compounds. The
acid-functional porous sorbent is derived from a porous
(e.g., microporous, mesoporous, or macroporous) sorbent
material. The acid-functional nonwoven fibrous substrate
functions as a scaffold for one or more acids wherein such
acids are covalently attached thereto. Optionally, each of an
acid-functional porous sorbent and an acid-functional non-
woven fibrous substrate may be used in the same sensor.

Suitable acids include acid compounds or acid moieties
having a boiling point above 120° C. and a pKa of no greater
than 2.5. Examples of acid compounds that may be incor-
porated into the porous sorbent include trichloroacetic acid,
sulfuric acid, phosphoric acid, alkyl sulfonic acid (e.g.,
methanesulfonic acid), alkyl phosphonic acid (e.g., metha-
nephosphonic acid), benzene sulfonic acid, and toluene
sulfonic acid. These acids may be used individually or in any
combination. In this context, "alkyl" refers to C1-C4 alkyl
groups, with methyl and ethyl being preferred. Examples of
acid moieties (i.e., acid groups) that may be covalently
attached to the porous sorbent or nonwoven fibrous substrate
include sulfonic acid ($-SO_3H$) and phosphonic acid
($-PO_3H_2$) groups. Various combinations of acid com-
pounds and acid moieties may be used as desired.

In certain embodiments, the acid-functional porous sor-
bent is present in an amount of at least 10 grams per square
meter (gsm), at least 20 gsm, or at least 40 gsm, of an area
of the sensor on which the sorbent is disposed. In certain
embodiments, the acid-functional porous sorbent is present
in an amount of up to 1000 gsm, up to 600 gsm, up to 400
gsm, or up to 250 gsm, of an area of the sensor on which the
sorbent is disposed.

In certain embodiments, if the acid is in the form of acid
moieties (i.e., acid groups) that are covalently attached to the
porous sorbent to form the acid-functional porous sorbent,
they are present in an amount of at least 0.2 millimole acid moieties per gram of acid-functional porous sorbent
(mmole/g), at least 0.5 mmole/g, at least 1 mmole/g, or at
least 2 mmole/g (millimoles of acid moieties per gram of
acid-functional porous sorbent); and up to 5.5 mmole of acid
moieties per gram of acid-functional porous sorbent. In
certain embodiments, if the acid is in the form of acid
moieties (i.e., acid groups) that are covalently attached to the
nonwoven fibrous substrate to form the acid-functional
porous sorbent, they are present in an amount of at least 0.5
millimole acid moieties per gram of acid-functional nonwo-
ven fibrous substrate (mmole/g), at least 1.0 mmole/g, at
least 1.5 mmole/g, at least 2 mmole/g, or at least 2.5
mmole/g (millimoles of acid moieties per gram of acid-
functional nonwoven fibrous substrate); and up to 4 mmole
of acid moieties per gram of acid-functional nonwoven
fibrous substrate.

In certain embodiments, if the acid is an acid compound
impregnated in the porous sorbent to form the acid-func-
tional porous sorbent, it is present in an amount of at least
5 percent by weight (wt. %), at least 10 wt. %, or at least 20
wt. % based on the total weight of the acid-functional porous
sorbent. In certain embodiments, if the acid is an acid
compound impregnated in the porous sorbent to form the
acid-functional porous sorbent, it is present in an amount of
up to 80 wt. %, up to 70 wt. %, or up to 60 wt. %, based on
the total weight of the acid-functional porous sorbent.

The "porous" sorbent includes minute spaces or holes
through which liquid or air may pass. It may include a
microporous, mesoporous, or macroporous material. A mes-
oporous material is a material having pores with diameters
of 2 nanometers to 50 nm, a microporous material is a
material having pores smaller than 2 nm in diameter, and a
macroporous material is a material having pores larger than
50 nm in diameter. The amount of nitrogen gas absorbed by
the porous sorbent under cryogenic conditions at a relative
pressure of 0.98 may be used to measure the total pore
volume for pores having diameters up to 50 nanometers.
This method measures both micropores and mesopores. The
pore volume of the porous sorbent at a relative pressure of
0.98 is often at least 0.2 $cm^3$/gram, at least 0.4 $cm^3$/gram, at
least 0.6 $cm^3$/gram, at least 0.8 $cm^3$/gram, at least 1.0
$cm^3$/gram, or at least 1.2 $cm^3$/gram; and no more than 2.5
$cm^3$/gram. In some embodiments, the pore volume of the
porous sorbent is substantially macroporous and has quite
low microporosity and mesoporosity.

Nonwoven fibrous substrates are formed of a plurality of
fibers, for instance and without limitation, fibers comprising
polypropylene, polyethylene terephthalate (PET), polylactic
acid (PLA), polyphenylene sulfide (PPS), or any combina-
tion thereof. Suitable nonwoven fibrous substrates may be
formed using melt blowing, melt spinning, electrospinning,
plexifilament formation, gas jet fibrillation, fiber splitting, or
a combination thereof. Acid-functional nonwoven webs may
be suitably prepared by grafting functional monomers onto
the surface of the fibers of the nonwoven fibrous substrates.
The functionalization can be accomplished, in general, by
first e-beaming the nonwoven fibrous substrates and then
soaking them in a monomer solution. Suitable monomers
include sulfonic and phosphonic acid-functional free-radi-
cally polymerizable monomers, such as 2-acrylamido-2-
methylpropane sulfonic acid (AMPS), vinyl sulfonic acid,
and 4-styrene sulfonic acid. In some cases, one or more
additional monomers may also be included, such as the
neutral and epoxy monomers described in detail in PCT
Application No. IB2022/051648. Preferably, when an acid-
functional nonwoven fibrous substrate is employed with a
heat-shrinkable film, up to 100% of the area of the heat-shrinkable film, such as no more than 60% of the area of the heat-shrinkable film, no more than 50%, no more than 40%, or no more than 30% of the area of the heat-shrinkable film, no more than 20%, or no more than 10% is covered by one or more pieces of the acid-functional nonwoven fibrous substrate to allow enhanced visible observation of the extent of film shrinkage.

Porous sorbents include those that can withstand the acids described herein without degradation. They may include inorganic materials, organic materials, or combinations thereof. Examples include activated carbon, porous silica, zeolites, and porous organic polymers. Either individual porous sorbents or any combination of porous sorbents may be used if desired.

In certain embodiments, the porous sorbents include porous organic polymers. In certain embodiments, the porous organic polymers are derived from at least 60 wt. % aromatic monomers. Exemplary porous organic polymers include styrene-divinylbenzene, divinylbenzene-maleic anhydride (such as those described in International Publication No. WO 2017/106434 (3M Innovative Properties Co.)), and other aromatic-containing polymers. Combinations of porous sorbents may be used if desired. In certain embodiments, the porous organic polymers may be functionalized with sulfonic acid groups or other acid moieties as described herein. A precursor polymeric material (one type of porous sorbent material) that is reacted with an agent that provides such groups (e.g., an acid functionalizing agent such as a sulfonic acid agent) to form the acid-functional porous sorbent is typically formed from a polymerizable composition that contains aromatic monomers. Examples of aromatic monomers include, but are not limited to, styrene, styrene substituted with an alkyl group, divinylbenzene (DVB), and the like. Other examples of aromatic monomers include styrene substituted with a chloromethyl group (e.g., vinylbenzyl chloride). Other examples of aromatic monomers include bis(chloromethyl)-substituted aromatic monomers (e.g., p-xylylene-dichloride or isomers thereof). In some embodiments, at least 60 wt. %, at least 70 wt. %, at least 80 wt. %, at least 85 wt. %, at least 90 wt. %, or at least 95 wt. %, and up to 100 wt. %, up to 99 wt. %, up to 98 wt. %, up to 95 wt. %, or up to 90 wt. % of the monomers in the polymerizable composition are aromatic monomers.

The precursor polymeric material is typically crosslinked, thereby forming one type of porous sorbent. Crosslinking tends to enhance the porosity of the precursor polymeric materials and the resulting acid-functional porous sorbent. Any crosslinking method can be used. For example, in some embodiments, the polymerizable composition contains relatively large amounts of DVB (e.g., at least 10 wt. %) and no post-polymerization crosslinking is used. In other embodiments, the precursor is crosslinked lightly by the addition of relatively low amounts of DVB (e.g., 1 wt. % to less than 10 wt. %) in the polymerizable composition. Further crosslinking occurs post-polymerization using Friedel-Crafts chemistry in the presence of compounds having chloromethyl groups or chloromethylether groups such as, for example, xylylene-dichloride (XDC), 1,4-bischloromethyldiphenyl (CMDP), monochlorodimethylether (MCDE), tris-(chloromethyl)-mesitylene (CMM), and p,p'-bis-chloromethyl-1, 4-diphenylbutane (DPB). In still other embodiments, the precursor polymeric material can be crosslinked using predominately Friedel-Crafts chemistry by reacting with a linear polymer such as polystyrene. The crosslinking of linear polymers such as polystyrene using Friedel-Crafts chemistry is described, for example, in the reference V. A. Davankov et al., *Reactive Polymers,* 13, 27-42 (1990). A small molecule crosslinker having chloromethyl or chloromethyl ether groups is added. This reference also describes the post-crosslinking of gel-type polymers (e.g., lightly crosslinked polymers such as polystyrene crosslinked with low amounts of DVB such as 1 wt. %) using Friedel-Crafts chemistry.

Alternatively, gel-type polymers can be prepared from a monomer mixture of styrene and vinylbenzyl chloride (VBC) that is crosslinked with low amounts of DVB such as 2 wt. % or less. The gel-type polymers can be crosslinked using Friedel-Crafts chemistry but no small molecule crosslinker having chloromethyl or chloromethyl ether groups is required. Rather, the chloromethyl group of VBC serves as the crosslinking point. That is, the crosslinker is already part of the gel-type polymer. This method is further described in the reference Jou-Hyeon Ahn et al., *Macromolecules,* 627-632 (2006).

Macroporous precursor polymeric materials can be prepared from a mixture of styrene and DVB by suspension, emulsion, or precipitation polymerization methods. In precipitation polymerization processes, styrene and DVB monomer mixtures are polymerized in the presence of various solvents that serve as porogens. This can also be accomplished using an emulsion or suspension polymerization method where the organic phase consists of the monomers and the porogen. With precipitation polymerization processes, the reaction product is a monolith that matches the size and shape of the container used for the polymerization reaction. With the emulsion or suspension processes, however, the final polymeric material is typically in the form of beads (particles). The porosity of the resulting polymeric material can be controlled by selection of the amount and identity of the porogen used, the solids content of the polymerization mixture (organic phase), and the amount of crosslinker (e.g., DVB) that is used.

These polymerization methods are further discussed in references such as the following: M. M. Mohamed et al., *Nanomaterials,* 2, 163-186 (2012); Y. Zhang et al., *Nano Today,* 4, 135-142 (2009); S. Wei et al., *Colloids and Surfaces A: Physiochem. Eng. Aspects,* 414, 327-332 (2012); A. K. Nyhus et al., *J. Poly. Sci. Part A: Polymer Chemistry,* 37, 3973-3990 (1999); Q. Liu et al., *J. Phys. Chem. C,* 112, 13171-13174 (2008); U.S. Pat. No. 3,531,463 (Gustafson et al.), and U.S. Pat. No. 6,416,487 B1 (Braverman et al.).

Other macroporous precursor polymeric materials can be formed using suspension or emulsion polymerization methods like those described above but with lower levels of the DVB crosslinker (e.g., 2 wt. % to 20 wt. %). A portion of the styrene monomers is replaced with VBC. The resulting polymers can be further crosslinked using Friedel-Crafts chemistry. This method is further described in the reference Jou-Hyeon Ahn et al, *Macromolecules,* 627-632 (2006).

Still other precursor polymeric materials can be prepared as discussed in the reference C. D. Wood et al., *Chem. Mater.,* 19, 2034-2048 (2007). In this instance, bis(chloromethyl) aromatic monomers such as p-xylylene-dichloride (XDC) or isomers thereof, 4,4'-bis(chloromethyl)-1,1'-biphenyl, and bis(chloromethyl) anthracene are reacted alone or in combination using Friedel-Crafts chemistry to produce micro-, meso-, and macroporous precursor polymeric materials for use as porous sorbents.

Alternatively, precursor polymeric materials can be prepared using even simpler aromatic compounds such as benzene and crosslinking the benzene using Friedel-Crafts chemistry and a small molecule crosslinker such as formaldehyde dimethyl acetal as described in B. Li et al., *Macromolecules*, 44, 2410-2414 (2011).

In some embodiments, the precursor polymeric material is formed from a polymerizable composition that contains 10 wt. % to 80 wt. % DVB and 20 wt. % to 90 wt. % styrene-type monomers (i.e., styrene and/or styrene substituted with an alkyl group) based on the total weight of monomers in the polymerizable composition. In many such embodiments, at least 90 wt. %, at least 92 wt. %, at least 95 wt. %, at least 96 wt. %, at least 98 wt. %, at least 99 wt. %, and up to 100 wt. % of the monomers in the polymerizable composition are selected from DVB or a styrene-type monomer. In some embodiments, the amount of DVB is at least 10 wt. %, at least 20 wt. %, at least 30 wt. %, at least 40 wt. %, at least 50 wt. %, at least 60 wt. %, and up to 80 wt. %, up to 70 wt. %, up to 60 wt. %, up to 50 wt. %, or up to 40 wt. %, based on the total weight of monomers in the polymerizable composition. The remainder of the monomers is often a styrene-type monomer.

The precursor polymeric material (and other porous sorbents) is typically porous and often has a BET specific surface area that is in a range of 25 square meters per gram ($m^2/g$) to 5000 $m^2/g$. The BET specific surface area is often at least 25 $m^2/g$, at least 50 $m^2/g$, at least 100 $m^2/g$, at least 200 $m^2/g$, at least 300 $m^2/g$, at least 400 $m^2/g$, or at least 500 $m^2/g$, and up to 5000 $m^2/g$, up to 3000 $m^2/g$, up to 1500 $m^2/g$, up to 1200 $m^2/g$, up to 1100 $m^2/g$, up to 1000 $m^2/g$, up to 900 $m^2/g$, up to 800 $m^2/g$, up to 700 $m^2/g$, up to 600 $m^2/g$, or up to 500 $m^2/g$. In some embodiments, BET specific surface area is in a range of 25 $m^2/g$ to 5000 $m^2/g$, or in a range of 50 $m^2/g$ to 1500 $m^2/g$. Such surface areas also apply to the acid-functional porous sorbents.

In certain embodiments, the precursor polymeric material is treated with an acid-functionalizing agent (e.g., sulfonic acid agent) to form an acid-functional polymeric material (a type of acid-functional porous sorbent). The acid group (e.g., sulfonic acid group ($—SO_3H$)) typically replaces a hydrogen atom that is bonded to a carbon atom that is part of an aromatic ring of the precursor polymer. Any known method can be used to introduce the acid group into the precursor polymeric material.

In some embodiments, the precursor polymeric material is reacted with a halogenated acid, such as a halogenated sulfonic acid (e.g., chlorosulfonic acid) acid-functionalizing agent. The precursor polymeric material is mixed with a solution of the halogenated acid dissolved in an appropriate organic solvent. Suitable organic solvents include various halogenated solvents such as 1,2-dichloroethane, methylene chloride, and chloroform. The precursor polymeric material is often added to the solution of the halogenated acid at a temperature below room temperature. The initial reaction can be quite exothermic so, if adequate care is not taken, the solvent can boil during the addition. After the reactants are combined, the temperature is often increased to any desired temperature such as room temperature up to the temperature associated with reflux conditions. The reaction time can range from a few minutes to 24 hours. After this reaction, the resulting intermediate polymeric material has attached halogenated acid-functional groups (e.g., $—SO_2X$ groups where X is halo such as chloro). The reaction time and the reaction temperature can be varied to prepare polymeric materials with different amounts of the acid (sulfonyl-containing) group.

To prepare the acid moiety (i.e., acid group), such as sulfonic acid group ($—SO_3H$), the intermediate polymeric material with attached halogenated acid-functional group (e.g., $—SO_2X$ group) is placed in water. The conversion of the halogenated groups to the acid groups often can occur at room temperature within 30 minutes, within 1 hour, within 2 hours, within 4 hours, within 8 hours, within 12 hours, within 24 hours, within 36 hours, within 48 hours, within 60 hours, or within 72 hours.

In other embodiments, the precursor polymeric material is reacted with concentrated sulfuric acid or with concentrated sulfuric acid in the presence of a catalyst such as silver sulfate. When a catalyst is present, the reaction typically proceeds faster. With or without the catalyst, the reaction temperature is often in a range of room temperature (e.g., 20-25° C.) to 150° C., in a range of room temperature to 125° C., or in a range of room temperature to 100° C. The reaction times can vary from a few minutes (e.g., 5 minutes, 10 minutes, or 30 minutes) to 24 hours or longer. As with halogenated sulfonic acid, the reaction time and the reaction temperature can be varied to prepare polymeric materials with different amounts of the sulfonic acid group. After this reaction, the resulting polymeric material has attached acid groups (e.g., $—SO_3H$ groups), thereby forming an acid-functional porous sorbent.

In certain embodiments, the acid-functional porous sorbent is encapsulated. To keep the acid-functional porous sorbent encapsulated, it may be combined with a binder and formed into a monolith or into a composite particle. The monolith or composite particle is placed in thermal contact with the thermal indicator component, thereby causing the acid-functional porous sorbent to be in thermal contact with the thermal indicator component. The composite construction can be placed in a pouch, for example, that includes holes for passage of the ethylene oxide. Alternatively, it can be placed in a container (e.g., physical pack) that defines a tortuous channel for passage of the ethylene oxide.

Heat-Shrinkable Film

Useful heat-shrinkable films (i.e., polymer sheets) are also known as shape-memory films (i.e., polymer sheets). Useful heat-shrinkable films may include physically and/or chemically crosslinked polymers.

Suitable physically crosslinked films include linear block copolymers such as thermoplastic polyurethane elastomers with hard segments and soft switching segments. Multi-block copolymers can also serve as films such as, for example, polyurethanes with polystyrene and poly(1,4-butadiene) blocks; ABA tri-block copolymers of poly(tetrahydrofuran) and poly(2-methyl-2-oxazoline); polyhedral oligomeric silsesquioxane (POSS)-modified polynorbornene; and polyethylene/Nylon-6 graft copolymers.

Suitable chemically crosslinked films include, but are not limited to, crosslinked high density polyethylene, crosslinked low-density polyethylene, and crosslinked copolymers of ethylene and vinyl acetate.

Other examples of heat-shrinkable films include polymers selected from polyurethanes, polynorbornenes, polyethers, polyacrylates, polyamides, polysiloxanes, polyether amides, polyether esters, trans-polyisoprenes, polymethyl methacrylates, crosslinked trans-polyoctylenes, crosslinked polyethylenes, crosslinked polycyclooctenes, inorganic-organic hybrid polymers, copolymer blends with polyethylene and styrene-butadiene co-polymers, urethane-butadiene copolymers, polymethyl methacrylate, polycaprolactone, and oligocaprolactone copolymers.

Suitable heat-shrinkable films include polymers such as those described in U.S. Pat. No. 5,506,300 (Ward et al); U.S. Pat. No. 5,145,935 (Hayashi); U.S. Pat. No. 5,665,822 (Bitler et al); U.S. Pat. No. 6,160,084 (Langer); U.S. Pat. No.

6,388,043 (Langer); U.S. Pat. No. 5,155,199 (Hayashi); U.S. Pat. No. 7,173,096 (Mather et al.); U.S. Pat. No. 4,436,858 (Klosiewicz); U.S. Pat. No. 6,423,421 (Banaszak); and U.S. Pat. Appl. Publ. Nos. 2005/244353 (Lendlein et al), U.S. 2007/009465 (Lendlein et al), and 2006/041089 (Mather et al).

Heat-shrinkable polymer films (sheets or rolls) can be processed by heating them to near or above the heat-shrinkable (i.e., shape-memory) transition temperature range of the particular material utilized, then orienting the sheet by stretching or tentoring it in at least one direction (typically down-web when a roll-to-roll process is used) followed by cooling the sheet to lock in the strain caused by the stretching. In some embodiments, the sheet can be oriented in two or more directions. For example, biaxially oriented films can be made by simultaneous down-web and cross-web stretching of the polymer film near or above its transition temperature range followed by cooling. Biaxially oriented films or sheets can have a maximum shrink tension in one direction.

The heat-shrinkable films of the sterilization sensors of the present disclosure reach a temperature at or above that which the shrink tension of the heat-shrinkable polymer is sufficiently high to cause a substantial change in one or more dimensions of the sheet. The process of making and orienting heat-shrinkable polymer sheets is well known to those having ordinary skill in the art.

In certain embodiments, the sterilization sensors of the present disclosure include a heat-shrinkable film with an area having a strained temporary shape and includes at least one of a plurality of perforations having a width therein and a total length. When heated to or above a transition temperature range, the heat-shrinkable polymer sheet at least partially converts from its strained temporary shape to its intrinsic shape. The intrinsic shape of the heat-shrinkable film is the shape to which it returns after the polymer is heated to or above a transition temperature range.

In certain embodiments, it is possible to anneal some heat-shrinkable polymers by heating them to a temperature close to but below the transition temperature range. Depending upon the composition of the polymer, such annealing can cause the temporary shape of the heat-shrinkable polymer to change and substantially eliminate the potential for small changes in shape at temperatures below the shape memory transition temperature range.

Examples of commercially available thermoplastic films include: polyurethanes available under the trade designation DIARY, including the MM, MP, MS, and MB (microbead powder) types series available from SMP Technologies, Inc. of Tokyo, Japan; elastic memory composites available under the trade designation EMC from Composite Technology Development, Inc. of Lafayette, CO; and polymers available under the trade designation VERIFLEX from Cornerstone Research Group, Inc. of Dayton, OH. The shape memory properties of acrylonitrile-butadiene-styrene (ABS) copolymers, polycarbonate, and polyethylene terephthalate are also disclosed by Hussein et al., in "New Technologies for Active Disassembly: Using the Shape Memory Effect in Engineering Polymers, *J. Product Development*, 6, 431-449 (2008).

Additional examples of commercially available heat-shrinkable films that can be converted into various shapes include those heat-shrinkable films available under the trade designations CORTUFF, CRYOVAC, and OPTI from Sealed Air Inc. of Elmwood Park, NJ Additional examples include heat-shrinkable films available under the trade designations SHRINKBOX, VHG, EZ, AFG, ABL and PLAnet from Bemis Clysar of Oshkosh, Wisc.

Optional Adhesive

In certain embodiments, the acid-functional porous sorbent or the acid-functional nonwoven porous substrate is adhered to the thermal indicator component using a layer of an adhesive. The layer of adhesive may be continuous or discontinuous. It may be laminated to the thermal indicator component or coated thereon (e.g., pattern coated). It may be a double-sided transfer adhesive, a sprayable adhesive, or a hot-melt adhesive.

Exemplary adhesives include those described, for example, in U.S. Pat. No. 7,893,179 (Anderson et al.) and U.S. Pat. No. 9,134,251 (Thomas et al.). For example, the adhesive may include a natural rubber adhesive, a synthetic rubber adhesive, a poly-alpha-olefin adhesive, a styrene block copolymer adhesive, a poly(meth)acrylate adhesive, a silicone adhesive, or mixtures thereof.

The layer of adhesive can function as a buffer or insulator. Thus, the thickness of the adhesive can be tailored to control the extent of thermal response. A typical adhesive layer thickness is at least 1 micron, or at least 25 microns, and often up to 2500 microns, or up to 200 microns.

Exemplary Ethylene Oxide Sterilization Sensors

The ethylene oxide sterilization sensors can be incorporated into formats of known sterilization sensors. For example, U.S. Pat. No. 4,138,216 (Larsson et al.) discloses an ethylene oxide sterilization sensor, and U.S. Pat. No. 4,448,548 (Foley) and U.S. Pat. No. 5,378,430 (Nieves et al.) disclose steam sterilization sensors, which can be adapted to include the thermal indicator component(s) and acid-functional porous sorbent or acid-functional nonwoven fibrous substrate as disclosed herein. Other known sterilization sensors can be adapted by one of skill in the art, including, for example, U.S. Pat. No. 5,451,372 (Larsson et al.), U.S. Des 315,600 (Niven), and RE 34,515 (Foley). Sensors of the present disclosure can be in a variety of shapes and sizes. Typical sensors include a smallest dimension of at least 2.5 centimeters, to avoid getting lost in a sterilizer.

FIGS. 1-7 are representative ethylene oxide sterilization sensors.

Figure 1B:
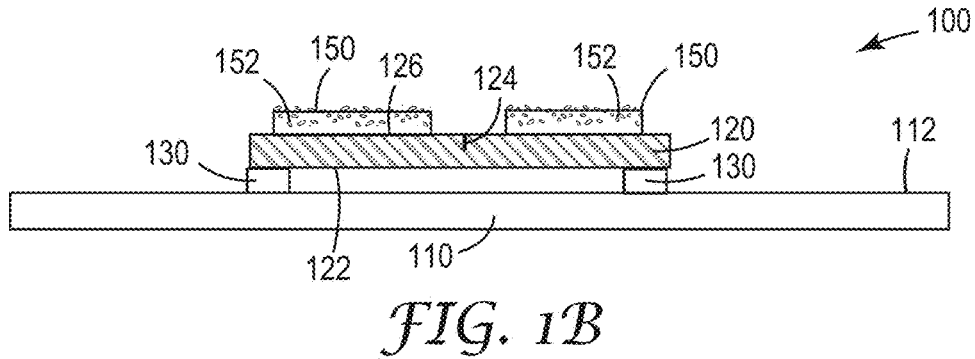
FIG. 1B is a cross-section of the EO sterilization sensor of FIG. 1a, along lines 1b-1b.

FIG. 1*a* is a schematic top view of an exemplary ethylene oxide sterilization sensor 100 according to the present disclosure, before activation by ethylene oxide. FIG. 1B is a cross-section of the ethylene oxide sterilization sensor 100 of FIG. 1*a*, along lines 1*b*-1*b*. Referring to FIGS. 1*a* and 1*b*, an ethylene oxide sterilization sensor 100 includes a substrate 110 having a major surface 112. A heat-shrinkable film 120 is attached to the major surface 112 of the substrate by an adhesive 130 (not visible in FIG. 1*a*). In this case, two spaced strips of adhesive 130 are provided, each attached to a first major surface 122 (not visible in FIG. 1*a*) of the heat-shrinkable film 120 and extending approximately parallel to an opposing edge of the heat-shrinkable film 120. A space is defined between the two lines of adhesive 130 in which the heat-shrinkable film 120 is not adhered to the substrate 110 and the adhesive 130 locks the heat-shrinkable film 120 in place at both ends of the sensor 100, which causes any shrinkage to move toward the immobilized ends in a generally linear fashion. Further, a perforated line 124 is provided down the center of the heat-shrinkable film 120 to provide a point of weakness within the heat-shrinkable film 120. The ethylene oxide sterilization sensor 100 also includes a line of a conductive ink 140 (not visible in FIG. 1B) as a thermal indicator component, which is disposed on a second major surface 126 of the heat-shrinkable film 120 orthogonal to the perforated line 124. Additionally, the ethylene oxide sterilization sensor 100 includes two spaced strips of adhesive 150, which an acid-functional sorbent 152 is disposed thereon and/or incorporated therein. The adhesive 150 provides thermal contact between the particles of acid-functional sorbent 152 and the heat-shrinkable film 120. Each strip of adhesive 150 is disposed on the second major surface 126 of the heat-shrinkable film 120 and extending approximately parallel to an opposing edge of the heat-shrinkable film 120.

Figure 1C:
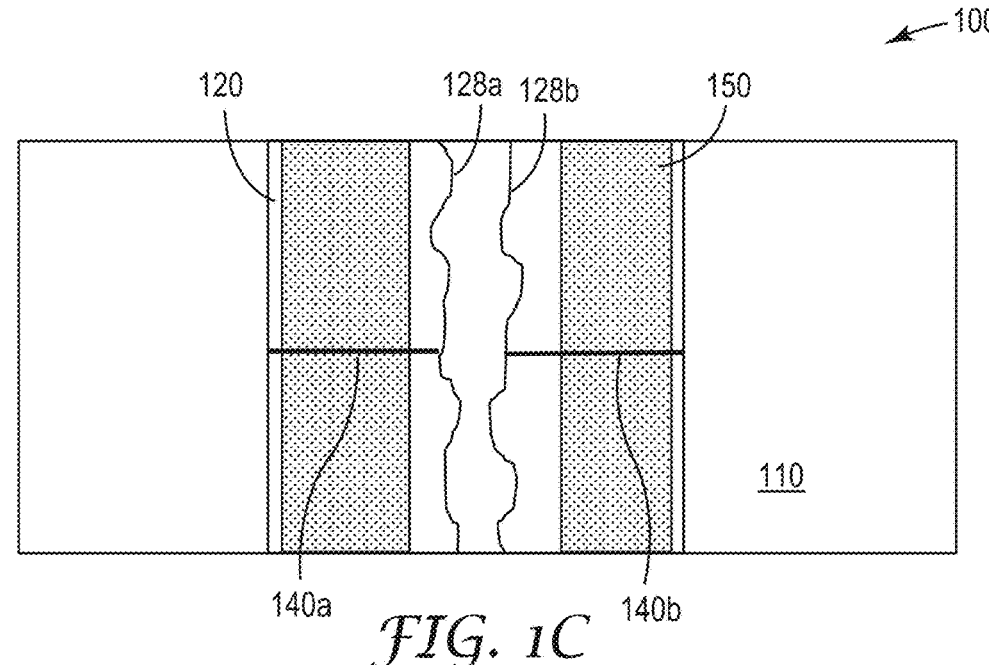
FIG. 1c represents the sterilization sensor after activation by EO.

In operation, the ethylene oxide sterilization sensor 100 is exposed to ethylene oxide, and once the acid of the acid-functional sorbent 152 reacts with a sufficient amount of ethylene oxide, the exothermic interaction generates sufficient heat to cause a dimensional change (i.e., shrinkage) in the heat-shrinkable film 120. FIG. 1c is a schematic top view of the ethylene oxide sterilization sensor 100 of FIG. 1a after activation by ethylene oxide. More particularly, the ethylene oxide sterilization sensor 100 of FIG. 1c shows that sufficient dimensional change (i.e., shrinking) of the heat-shrinkable film 120 results in failure of the heat-shrinkable film 120 at the perforated line 124, splitting the heat-shrinkable film 120 into separate pieces, each having an edge 128a and 128b spaced apart from each other and revealing the backing substrate 110 (which optionally can have a different color than the heat-shrinkable film 120 in at least its center region for easy visualization) after conditions for ethylene oxide sterilization have been met. The separation of the heat-shrinkable film 120 into two pieces also separates the line of conductive ink 140 into two partial lines of conductive ink 140a and 140b. The degree of shrinkage and separation between the two pieces of the heat-shrinkable film 120 will depend on the amount of heat to which it is exposed, which is, in part, a function of how much ethylene oxide to which the sensor has been exposed. The ethylene oxide sterilization sensor 100 of this embodiment includes the options of both a visible detectable result with the breakage of the heat-shrinkable film 120 into two pieces and an electronic detectable result with the breakage of the line of conductive ink 140 that destroys an electronic circuit that could be connected to the line of conductive ink 140.

Figure 2A:
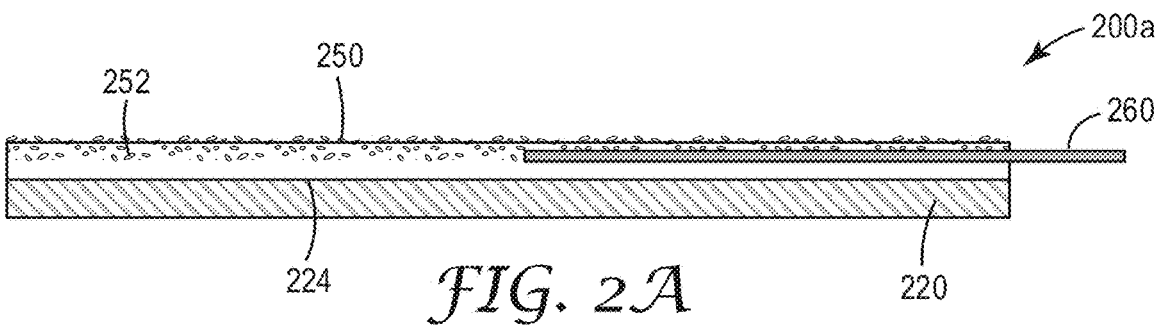
FIG. 2a is a schematic cross-sectional view of another exemplary EO sterilization sensor according to the present disclosure.

Referring to FIG. 2a, a schematic cross-sectional view is provided of another exemplary ethylene oxide sterilization sensor 200a according to the present disclosure. The ethylene oxide sterilization sensor 200a includes a substrate 220 having a major surface 224. The substrate 220 is not particularly limited, and may be or comprise, for instance, plastic film, glass, thin aluminum film, molded plastic sheet paper, foil, etc. For sensors that will be applied to a surface that is not flat, a conformable substrate material is preferable. An adhesive 250 is disposed on at least a portion of the major surface 224 of the substrate 220, the adhesive 250 having particles of an acid-functional sorbent 252 disposed thereon and/or incorporated therein. The ethylene oxide sterilization sensor 200a further includes a thermocouple 260 as a thermal indicator component, which is partially embedded in the adhesive 250.

Figure 2B:
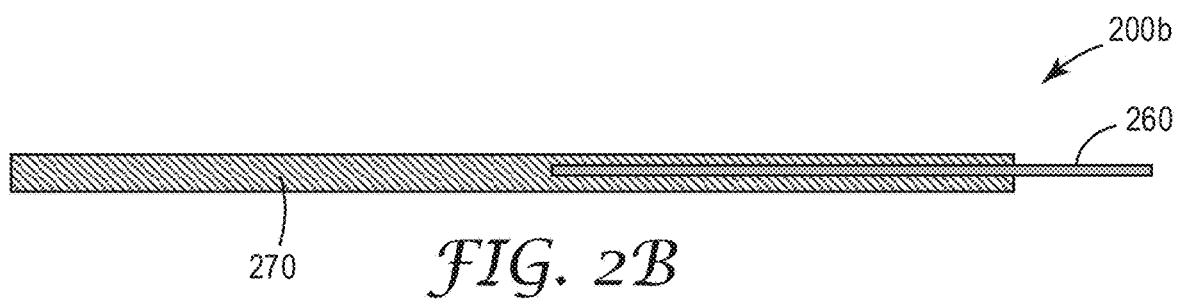
FIG. 2b is a schematic cross-sectional view of an additional exemplary EO sterilization sensor according to the present disclosure.

Referring to FIG. 2b, a schematic cross-sectional view is provided of an additional exemplary ethylene oxide sterilization sensor 200b according to the present disclosure. The ethylene oxide sterilization sensor 200b includes an acid-functional nonwoven fibrous substrate 270 and a thermocouple 260 as a thermal indicator component, which is partially embedded in the acid-functional nonwoven fibrous substrate 270. Alternatively, the thermocouple 260 could be attached to a major surface of the acid-functional nonwoven fibrous substrate 270 using an adhesive or a physical attachment means (e.g., a clamp or a clip). Optionally, a second substrate (not shown) could be used with the ethylene oxide sterilization sensor 200a or the ethylene oxide sterilization sensor 200b. For instance, a major surface of the substrate 220 (that is opposite the major surface 224) could be adhered to a second substrate, (e.g., glass, a thin aluminum film, molded plastic sheet, paper, foil, etc.). Similarly, the acid-functional nonwoven fibrous substrate 270 could be adhered to a second substrate.

In operation, the ethylene oxide sterilization sensor 200a or 200b is exposed to ethylene oxide, and once the acid of the acid-functional sorbent 252 or the acid of the acid-functional nonwoven fibrous substrate 270, respectively, reacts with a sufficient amount of ethylene oxide, the exothermic interaction generates sufficient heat to cause a detectable response from the thermocouple 260. The skilled practitioner will understand that the thermocouple needs to be attached to some type of electronics to obtain and display temperature measurements from the thermocouple (such as a data acquisition system from Keysight Technologies, Colorado Springs, CO).

Figure 3:
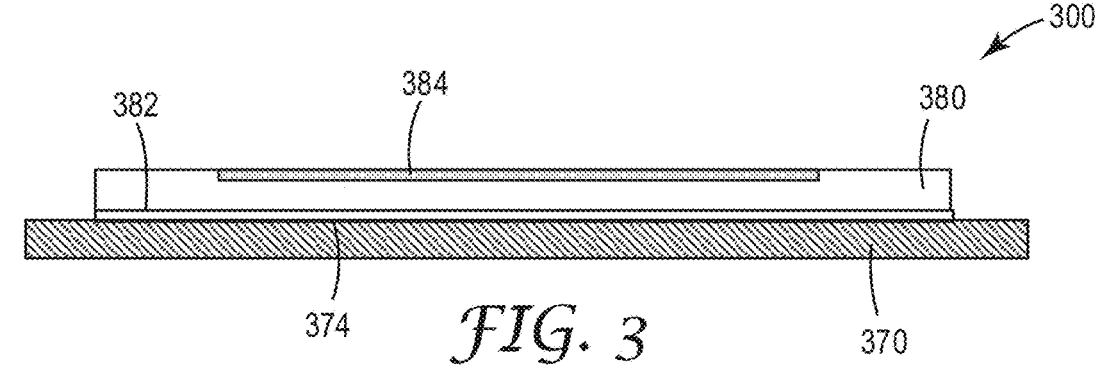
FIG. 3 is a schematic cross-sectional view of a further exemplary EO sterilization sensor according to the present disclosure.

Referring to FIG. 3, a schematic cross-sectional view is provided of a further exemplary ethylene oxide sterilization sensor 300 according to the present disclosure. The ethylene oxide sterilization sensor 300 includes an acid-functional nonwoven fibrous substrate 370 and an irreversible temperature indicator 380 disposed on a major surface 374 of the acid-functional nonwoven fibrous substrate 370. One suitable irreversible temperature indicator includes a multiple-point temperature-indicating label comprising a thermochromic dye. In the embodiment shown in FIG. 3, the irreversible temperature indicator 380 includes an adhesive backing 382 that adheres the irreversible temperature indicator 380 to the major surface 374 of the acid-functional nonwoven fibrous substrate 370. The irreversible temperature indicator 380 further includes a display region 384 where a change in temperature can be observed. Optionally, a substrate (not shown) could be attached to at least a portion of a major surface of the acid-functional nonwoven fibrous substrate 370 opposite the major surface 374 to provide additional structural integrity to the ethylene oxide sterilization sensor 300.

Figure 4:
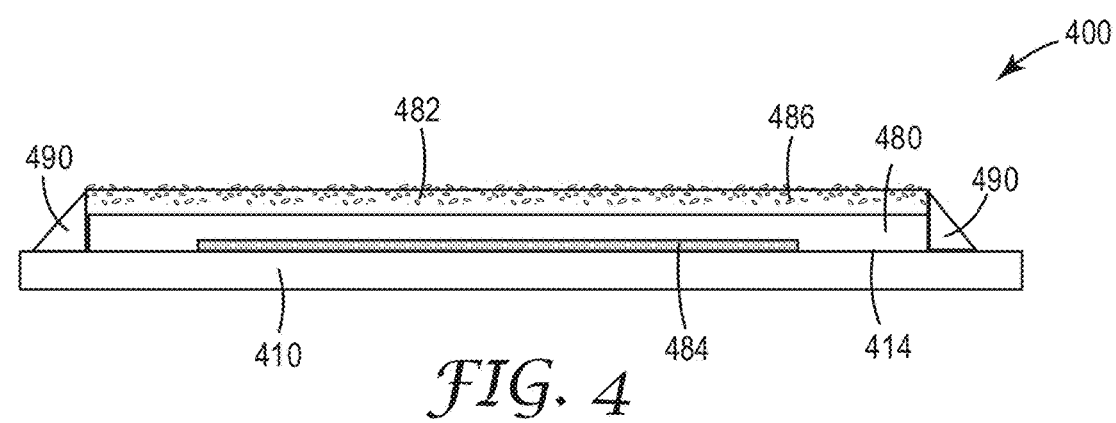
FIG. 4 is a schematic cross-sectional view of yet another exemplary EO sterilization sensor according to the present disclosure.

Referring to FIG. 4, a schematic cross-sectional view is provided of yet another exemplary ethylene oxide sterilization sensor 400 according to the present disclosure. The ethylene oxide sterilization sensor includes a substrate 410 having a major surface 414. An irreversible temperature indicator 480 is disposed on a major surface 414 of the substrate 410. In this embodiment, the irreversible temperature indicator 480 is adhered to the major surface 414 of the substrate 410 using adhesive 490 on opposing side edges of the irreversible temperature indicator 480. The irreversible temperature indicator 480 includes a display region 484 where a change in temperature can be observed, and the display region 484 faces the substrate 410. Preferably, a material is chosen for the substrate 410 that can be seen through by a user, such as glass or a transparent plastic, although the irreversible temperature indicator 480 could be removed from the substrate for observation of any temperature change. The irreversible temperature indicator 480 further includes an adhesive backing 482 having particles of an acid-functional sorbent 486 disposed thereon and/or incorporated therein. Optionally, additional adhesive (not shown) may be required to attach the irreversible temperature indicator to an object in the sterilizer chamber In operation, the ethylene oxide sterilization sensor 300 or 400 is exposed to ethylene oxide, and once the acid of the acid-functional nonwoven fibrous substrate 370 or the acid of the acid-functional sorbent 486, respectively, reacts with a sufficient amount of ethylene oxide, the exothermic interaction generates sufficient heat to cause a detectable response in the irreversible temperature indicator 480. In some cases, the display region 484 of the irreversible temperature indicator 480 comprises a series of areas (e.g., squares, circles, etc.), each labeled with a temperature, and as the heat rises, the areas representing increasingly higher temperatures show a response (e.g., changing from blank (such as white) to filled (such as black).

Figure 5:
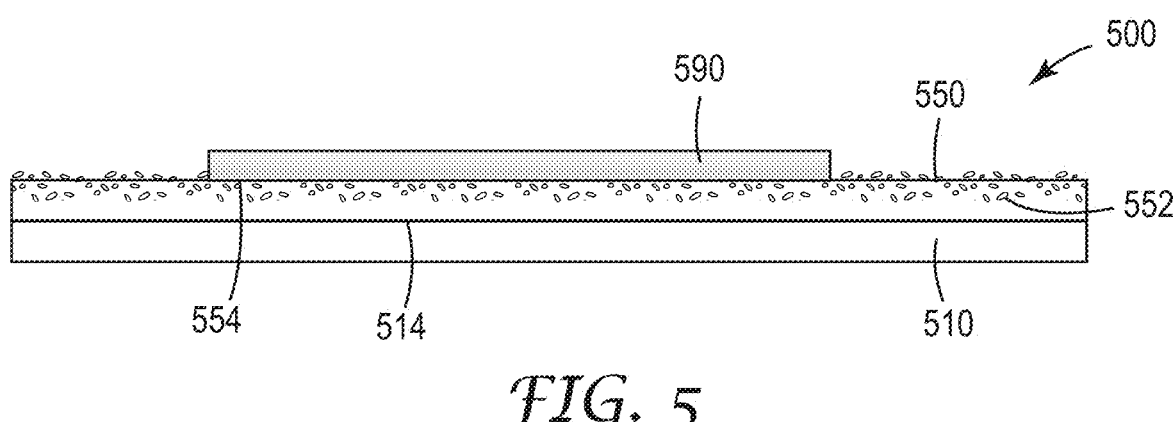
FIG. 5 is a schematic cross-section view of a still further exemplary EO sterilization sensor according to the present disclosure.

Referring to FIG. 5, a schematic cross-sectional view is provided of a still further exemplary ethylene oxide sterilization sensor 500 according to the present disclosure. The ethylene oxide sterilization sensor 500 includes a substrate 510 having a major surface 514. An adhesive 550 is disposed on at least a portion of the major surface 514 of the substrate 510, the adhesive 550 having particles of an acid-functional sorbent 552 disposed thereon and/or incorporated therein. The ethylene oxide sterilization sensor 500 further includes an RFID tag 590 as a thermal indicator component, which is in thermal contact with (e.g., disposed on) a major surface 554 of the heat transfer adhesive 550. In operation, the ethylene oxide sterilization sensor 500 is exposed to ethylene oxide, and once the acid of the acid-functional sorbent 552 reacts with a sufficient amount of ethylene oxide, the exothermic interaction generates sufficient heat to damage the electronic circuitry of the RFID tag 590. When an RFID reader no longer receives a signal from the RFID tag 590 or provides an altered response to the RF reader in response to heat to provide a detectable response, the ethylene oxide sterilization sensor 500 has indicated that conditions for ethylene oxide sterilization have been met.

Optionally, an ethylene oxide sterilization sensor according to the present disclosure may also include a transparent film (e.g., thermoplastic film) disposed on an element that does not generate a significant amount of heat, although this is optional. For instance, the topmost layer of a sensor can be a cover film (e.g., paper, thermoplastic film, etc.) that includes a window through which a portion of the ethylene oxide sterilization sensor that provides a visible result can be viewed. Such a window may simply be a cut-out creating an opening in the cover film.

Figure 6:
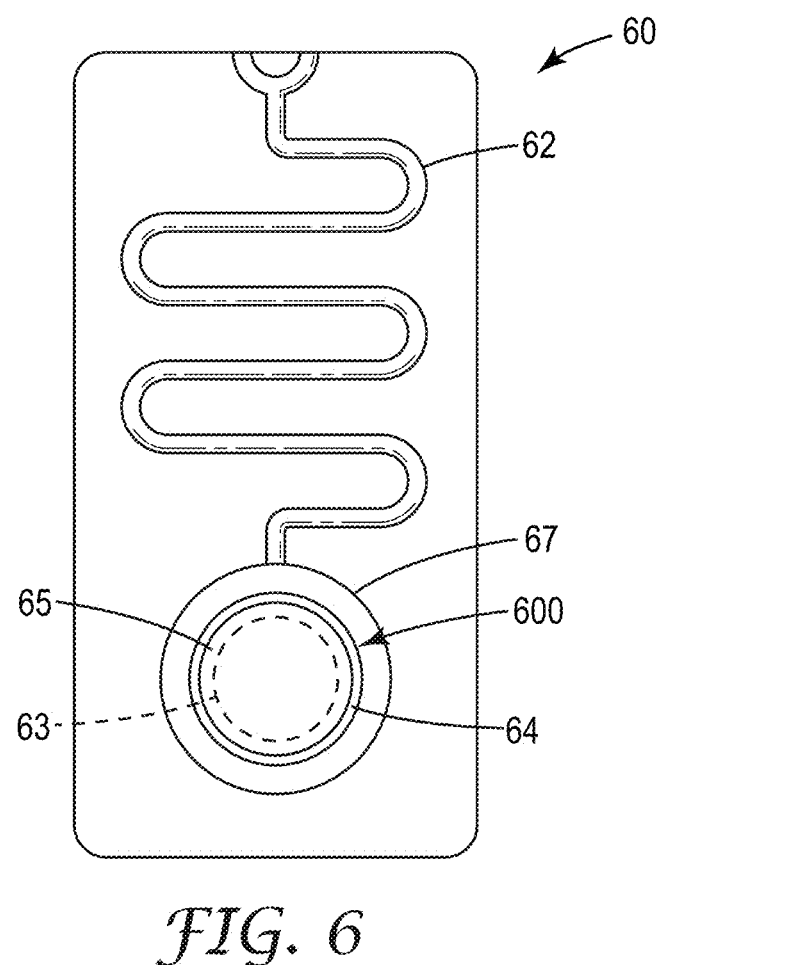
FIG. 6 is a schematic top view of a physical pack holding an EO sterilization sensor of the present disclosure.

Referring to FIG. 6, a schematic top view is provided of a physical pack 60 holding an embodiment of an ethylene oxide sterilization sensor 600 according the present disclosure. The physical pack 60 includes any ethylene oxide sterilization sensor 600 described herein. The physical pack 60 includes a molded backing (e.g., a thermoplastic backing) that includes a tortuous channel 62 and a reservoir 63, in which is placed the ethylene oxide sterilization sensor 600. An (optional) transparent film (e.g., transparent thermoplastic layer) is adhered to the molded backing to allow visualization of the change in the ethylene oxide sterilization sensor 600 for sensors that provide a visible result once conditions for ethylene oxide sterilization have been met. The tortuous channel 62 provides a passage through which the ethylene oxide diffuses through the physical pack 60 into the reservoir 63 where it contacts the ethylene oxide sterilization sensor 600. In this embodiment, the ethylene oxide sterilization sensor 600 includes a backing substrate 64 on which is disposed a visual indicator 63 (e.g., an image such as a picture or word, a colored feature, or an irreversible temperature indicator), such as a black circle, which represented by the dashed line in FIG. 6. While the sterilization sensor 600 is shown to be circular in this embodiment, any shape could be envisioned. Alternatively, the ethylene oxide sterilization sensor 600 could include an electronic thermal sensor in place of the visual indicator.

EXAMPLES

Objects and advantages of this invention are further illustrated by the following examples, but the particular materials and amounts thereof recited in these examples, as well as other conditions and details, should not be construed to unduly limit this invention. These examples are merely for illustrative purposes only and are not meant to be limiting on the scope of the appended claims. Unless otherwise stated, all amounts are in weight percent.

TABLE 1

| List of Materials and Suppliers. | | |
|---|---|---|
| DESIGNATION | DESCRIPTION | SOURCE |
| CER-1 | Cationic exchange resin obtained under the trade designation "AMBERLYST" 15H (>50 mesh/>300 micrometers (μm)) | Alfa Aesar, Ward Hill, MA |
| PP | Polypropylene 3860X (PP) | Total Petrochemicals USA, Inc., Houston, TX |
| AMPS | 2-Acrylamido-2-methylpropane sulfonic acid (AMPS) | Sigma-Aldrich, Milwaukee, WI |
| GMA | Glycidyl methacrylate (GMA) | Dow Chemical Company, Midland, MI |
| HCl | Hydrogen chloride (1.0N aqueous solution) | EMD Millipore Chemicals, Billerica, MA |
| Glass slide | Glass micro slide (2 inches × 3 inches; 5.1 centimeters (cm) × 7.6 cm) | Erie Scientific, Ramsey, MN |
| Transfer adhesive | 5 mil (0.13 millimeters (mm)) 200MP transfer adhesive, 2 inches (5.1 cm) wide | 3M Company, St. Paul, MN |
| Heat-shrink film | Polyethylene heat-shrink film obtained under the trade designation "CYLSAR SHRINKBOX 1525" | Bemis Company, Neenah, WI |
| Double coated tape | 6 mil (0.15 mm) 410M double coated tape | 3M Company, St. Paul, MN |

TABLE 1-continued

| List of Materials and Suppliers. | | |
| --- | --- | --- |
| DESIGNATION | DESCRIPTION | SOURCE |
| Silver ink | Silver nanoparticle dispersion (50-60 wt. %) in tetradecane obtained under the trade designation "SILVERJET DGH 55LT-25C" | Advanced Nano Products Co., Ltd., South Korea |

Test Methods

Procedure for Exposing Sensors to Ethylene Oxide

A Steri-Vac Sterilizer GSSX-1D manufactured by 3M Company (St. Paul, MN, USA) was used to expose all ethylene oxide (EO) sensor samples to sterilization conditions of EO to determine their response. A standard sterilization cycle was used in this experiment, which had exposure conditions of 55° C. at 50% Relative Humidity (RH) for 1 hour. A 4-100 EO cartridge was used to produce a concentration of approximately 735 milligram/liter (mg/L) of EO during the exposure.

EXAMPLES

Preparation of Polypropylene Nonwoven Fibrous Substrates

Polypropylene (PP) nonwoven fibrous substrates ("webs") having 9.9 μm effective fiber diameter (EFD), 102 grams per square meter (gsm) basis weight and 1.13 mm thickness were made using a melt-blowing process. The PP used was grade 3860X from Total Petrochemicals USA. The melt-blowing apparatus used consisted of a single screw extruder, a metering pump, and a melt-blowing die. The extruder used was a 5.1 cm single screw extruder (David Standard, Pawcatuck, CT). After the extruder, a positive displacement gear pump was used to meter and pressurize the polymer melt. The metered melt was sent to a drilled orifice melt-blowing die. Drilled orifice melt-blowing dies are described in U.S. Pat. No. 3,825,380 (Harding et al.). The die used was 50.8 cm wide with 25 polymer orifices per inch of width and each orifice being 381 μm in diameter. The die was operated at a temperature of 300° C. The air heater temperature was approximately 325° C. The air pressure was 31.0 kilopascals (kPa). The collector distance was 25.4 cm, and the collector speed was 2.2 meters/minute (m/min). The air gap was 762 μm, and the air knife set back was +254 μm. The air gap is the thickness of the air slots formed by the gaps between the air knives and die tip. The air knife set back is defined as the distance that the face of the air knives are set behind the apex of the die tip (i.e., a positive set back implies the apex of the die tip extends beyond the face of the air knives). The webs were collected on a vacuum collector and wound up onto cores using a surface winder. Effective fiber diameter (EFD) was measured using the technique described by Davies (Davies, C. N. *The Separation of Airborne Dust and Particles*, Inst. of Mech. Engineers, London, Proceedings 1B, 1952) for determining the average diameter of a fiber web using the air flow resistance, web thickness, and web basis weight. Air flow resistance was measured by recording the pressure drop of a 11.4 cm diameter web sample at an air flow rate of 85 liters/minute (L/min). Web thickness was measured on a 13.3 cm diameter circular web sample with an applied pressure of 150 Pascals (Pa). Web basis weight was measured by weighing a 13.3 cm diameter web sample. The equations described by Davies were then used to determine the EFD of the web.

Preparative Examples 1-4 (PE-1 TO 4): Preparation of Acid-Functional Nonwoven Fibrous Substrates Acid-functional nonwoven fibrous substrates ("webs") were prepared by grafting functional monomers onto the surface of the fibers of the nonwoven webs. The functionalization was accomplished, in general, by first e-beaming the nonwoven webs and then soaking them in a monomer solution. A series of four different acid functional nonwoven webs (PE-1-4) were prepared and varied only in the monomer mixture used to graft the functionalization onto the fibers. More specifically, four 20×20 cm nonwoven web samples were inserted individually into zip-top bags and transferred to a nitrogen inerted glove box. The sample bags were left open while the glove box chamber, bags, and contents were purged with nitrogen to less than 20 ppm oxygen as measured by a trace oxygen analyzer.

Each of the four zip-top bags was sealed and removed from the glove box. The four samples inside their purged bags were taped to a polyethylene terephthalate (PET) carrier web being conveyed at 5.5 m/min through an Energy Sciences, Inc. (Wilmington, MA) electron beam. Samples were irradiated at 300 kilovolts (kV) for a total dose of 10 Mrad.

Four monomer solutions were prepared by dissolving fixed amounts of glycidyl methacrylate (GMA) and 2-acrylamido-2-methylpropane sulfonic acid (AMPS) in deionized water in 4-ounce jars. The jars were capped and shaken by hand to mix the contents. Each jar was subsequently opened, and the solutions were sparged by bubbling nitrogen through each solution for 2 minutes. The jars containing these solutions were placed in the glove box.

After e-beaming, the sealed bags containing the samples were immediately placed in the glove box. The sparged monomer solutions were added to each of the bags, and the bags were resealed. A hand roller was run across each sealed bag to evenly distribute the monomer solution throughout the nonwoven web. The nonwoven webs were allowed to react with the monomer solutions for 3 hours. The reaction was stopped by removing the bags from the glove box and opening the bags to allow oxygen to quench the reaction.

Each acid functional nonwoven web was transferred to a stainless-steel pot of boiling water and extracted for 60 minutes to remove excess monomer solution and any free polymer. Each sample was removed from the boiling water and placed in a glass pan. Enough 1.0 N aqueous hydrogen chloride (HCl) was added to cover each sample. Each sample was left in the acid solution for one hour, removed from the acidic solution, and allowed to air dry in a hood. After drying, each sample was weighed to determine the mass increase and thus the yield of the grafting step. In Table 2, the compositions of the monomer solutions used to create the acid functional nonwoven web samples PE-1-4, the mass increase from grafting, and the yield of the grafting step are summarized.

TABLE 2

Composition of monomer solutions used to prepare acid functional nonwoven webs PE-1-4 and yields of grafting.

| Nonwoven Web | GMA, g | AMPS, g | Deionized Water, g | Mass Increase from Grafting, g | Monomer Grafted, % |
|---|---|---|---|---|---|
| PE-1 | 2.40 | 6.00 | 51.60 | 2.63 | 31 |
| PE-2 | 2.40 | 6.00 | 51.60 | 2.22 | 26 |
| PE-3 | 2.40 | 12.00 | 45.60 | 6.09 | 42 |
| PE-4 | 2.40 | 12.00 | 45.60 | 3.27 | 23 |

Examples 1-4: Preparation of Heat-Shrink Film Based Sensor Samples (EX-1A-D, EX-2A-D, EX-3A-D and EX-4A-D)

The following procedure was used to prepare sensor samples consisting of the acid functional nonwoven webs (PE-1-4) attached to heat-shrink film. A 15 cm wide strip of 200 MP transfer adhesive with the liner still on one side was laminated onto one side of the acid functional nonwoven web. A rubber roller was then used to press the adhesive into the web to ensure good adhesion by rolling over it several times. The desired geometry of the web to be used in the sensor was then cut out of the laminated stack. A 3.8×3.8 cm square was cut out from the heat-shrink film. The liner was removed from the transfer adhesive and the web applied, adhesive side down, to the square piece of the heat-shrink film in the layout desired. A roller was passed over the web several times to ensure complete contact of the adhesive with the heat-shrink film. A 1.3×1.3 cm square piece of 410M double coated tape (liner still on one side) was laminated to the center of the heat-shrink film side of the web. A roller was passed over the materials again to ensure proper lamination. The liner was removed from the 1.3×1.3 cm square piece of double coated tape, and the stack was laminated into the center of a 5×7.5 cm glass slide with the web being the top most layer. A roller was again passed over the sensor sample to ensure proper lamination of all the layers.

Figure 7A:
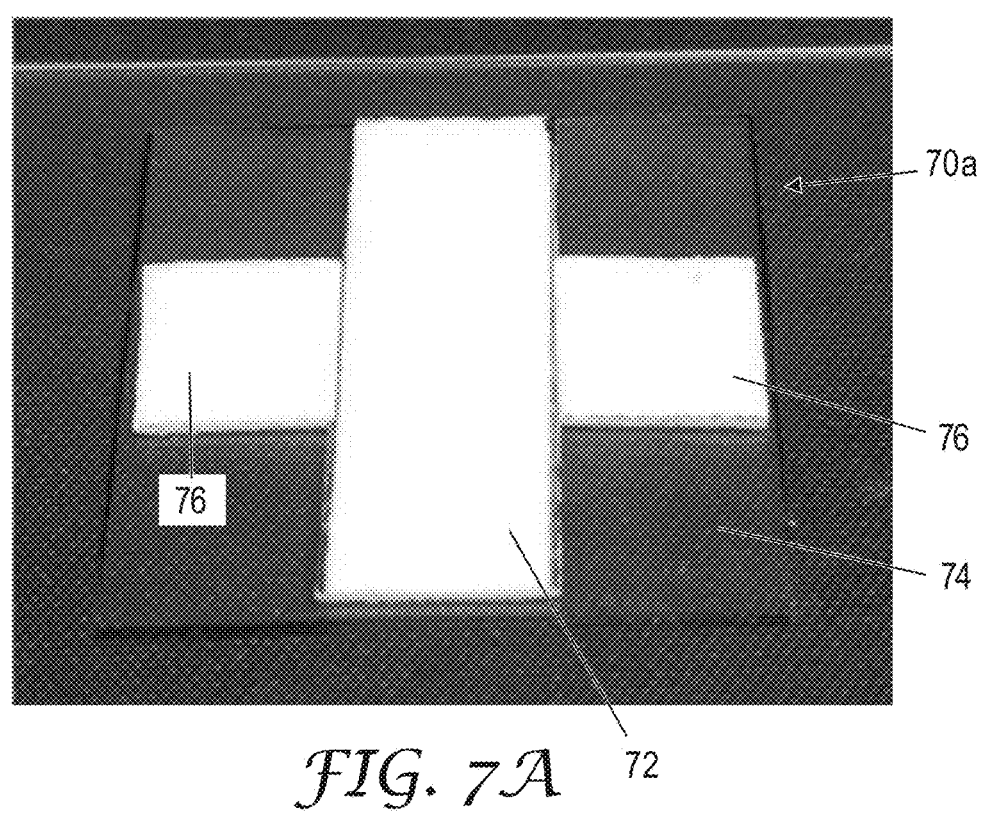
FIG. 7a is a photograph of the design of PE-1 of pattern A.
Figure 7B:
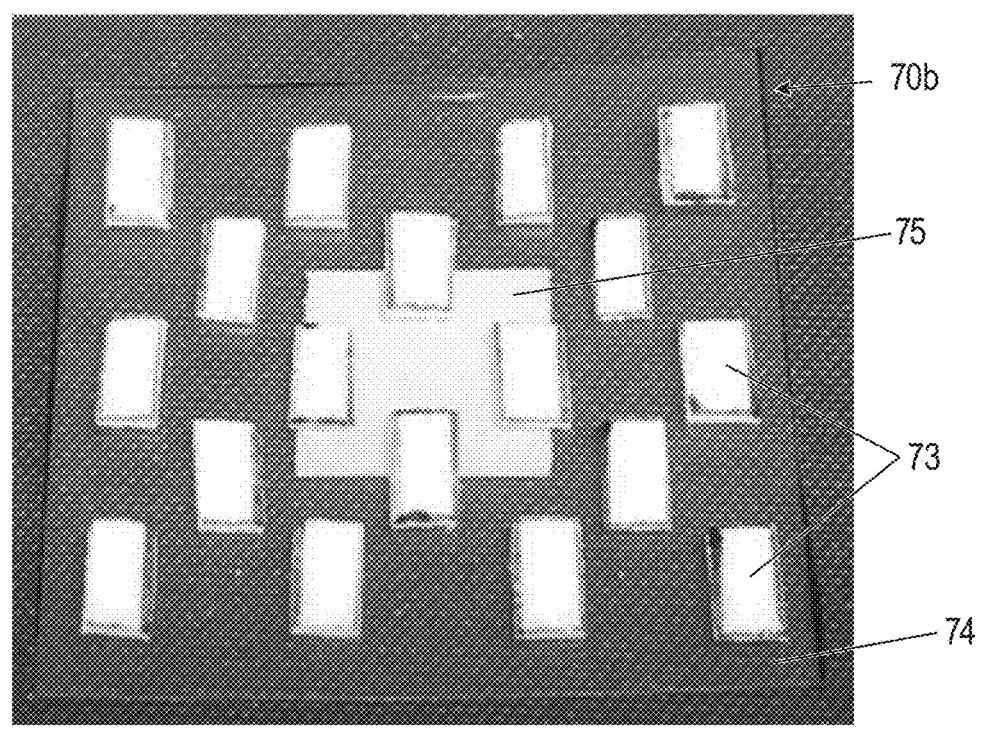
FIG. 7b is a photograph of the design of PE-2 of pattern B.
Figure 7C:
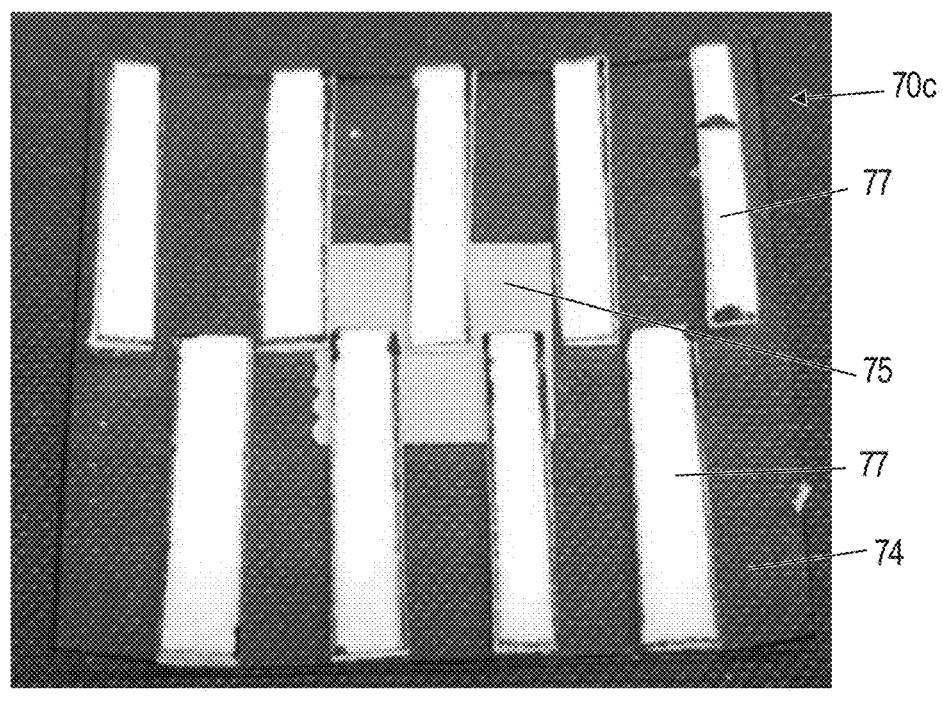
FIG. 7c is a photograph of the design of PE-3 of pattern C.
Figure 7D:
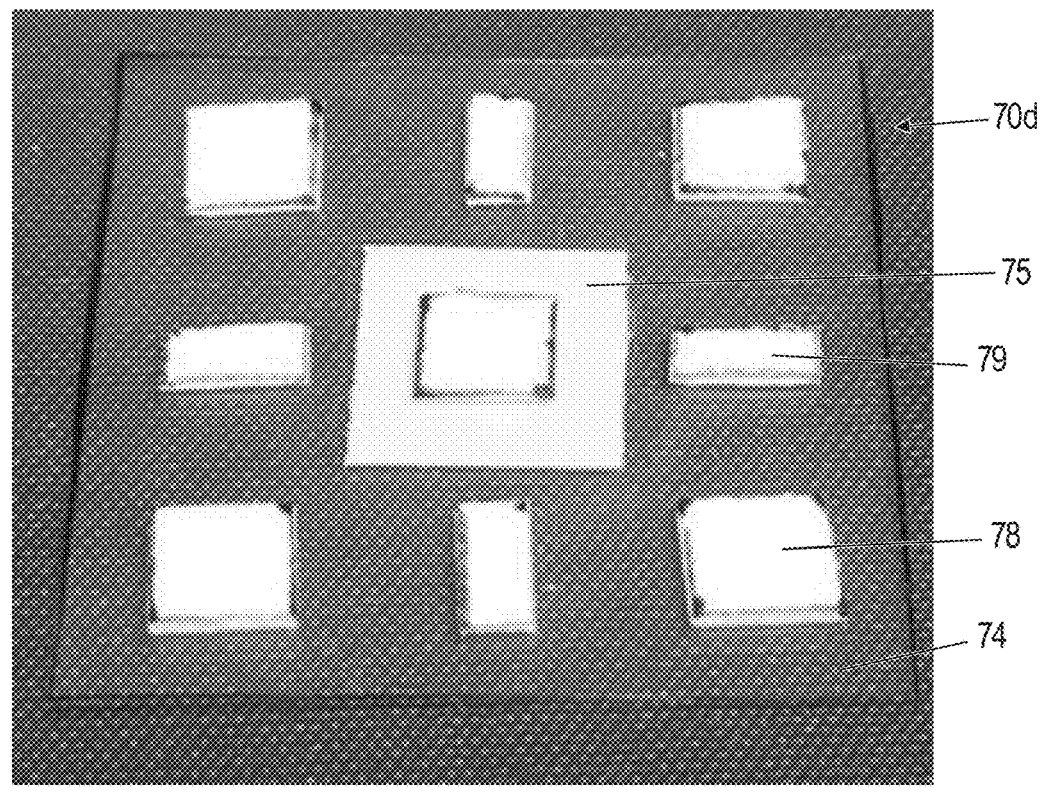
FIG. 7*d* is a photograph of the design of PE-4 of pattern D.

The design of the attachment of the acid functional nonwoven webs for each sensor sample is shown in FIGS. 7a-7d. In particular, the design of PE-1 is pattern A shown in FIG. 7a; the design of PE-2 is pattern B shown in FIG. 7b; the design of PE-3 is pattern C shown in FIG. 7c; the design of PE-4 is pattern D shown in FIG. 7d. Referring to FIG. 7a, the sensor sample 70a included one wide strip 72 of PE-1 adhered to the heat-shrink film 74 and two squares 76 of PE-1 adhered on either side of the wide strip 72 to form an overall pattern of a "plus" sign. Referring to FIG. 7b, the sensor sample 70b included a plurality of rectangular shaped pieces 73 of PE-2 each adhered to the heat-shrink film 74, with three rows having four separate pieces 73 alternating with two rows having three separate pieces 73. Referring to FIG. 7c, the sensor sample 70c included a plurality of long strips 77 of PE-3 each adhered to the heat-shrink film 74, with one row having five separate strips 77 and a second adjacent row having four separate strips 77. Referring to FIG. 7d, the sensor sample 70d included a plurality of square shaped pieces 78 and rectangular shaped pieces 79 of PE-4 each adhered to the heat-shrink film 74, with the square shaped pieces 78 in each corner and the center of the heat-shrink film 74 and the rectangular shaped pieces 79 spaced generally equally between the square shaped pieces 78. The square piece of 410M double coated tape 75 adhered to the opposite side of the heat-shrink film 74 is also visible in each of FIGS. 7b-7d.

The sensor samples were exposed to EO using the procedure described above (see Procedure for Exposing Sensors to Ethylene Oxide). In Table 3, the acid functional nonwoven web used, the web pattern used, the % of the area of the heat-shrink film covered by web, the amount of shrinkage in the X and Y direction after exposure and the total shrinkage after exposure for EX-1A-D, EX-2A-D, EX-3A-D and EX-4A-D are summarized.

TABLE 3

Summary of design and EO exposure results for EX-1A-D, EX-2A-D, EX-3A-D and EX-4A-D.

| EXAMPLE | Acid Functional Nonwoven | Nonwoven Web Pattern | Nonwoven Coverage, % | X-Axis Shrinkage, % | Y-Axis Shrinkage, % | Total Area Shrinkage, % |
|---|---|---|---|---|---|---|
| EX-1A | PE-1 | A | 56 | 8 | 4 | 12 |
| EX-1B | PE-1 | A | 32 | 8 | 8 | 16 |
| EX-1C | PE-1 | A | 38 | 8 | 8 | 16 |
| EX-1D | PE-1 | A | 19 | 8 | 8 | 16 |
| EX-2A | PE-2 | B | 56 | 13 | 13 | 23 |
| EX-2B | PE-2 | B | 32 | 8 | 8 | 16 |
| EX-2C | PE-2 | B | 38 | 8 | 13 | 20 |
| EX-2D | PE-2 | B | 19 | 13 | 8 | 20 |
| EX-3A | PE-3 | C | 56 | 33 | 25 | 50 |
| EX-3B | PE-3 | C | 25 | 21 | 25 | 41 |
| EX-3C | PE-3 | C | 29 | 50 | 25 | 63 |
| EX-3D | PE-3 | C | 19 | 25 | 17 | 38 |
| EX-4A | PE-4 | D | 56 | 13 | 17 | 27 |
| EX-4B | PE-4 | D | 25 | 13 | 25 | 35 |
| EX-4C | PE-4 | D | 38 | 17 | 13 | 27 |
| EX-4D | PE-4 | D | 19 | 13 | 13 | 24 |

Example 5 (EX-5): Preparation of Perforated Circuit Sensor

A perforated sensor was prepared by laminating two 0.6×3.8 cm strips of 410M double coated tape (liner still on one side) to opposite edges of a 3.8×3.8 cm square piece of heat-shrink film. The heat-shrink film was then flipped over, and a line of silver ink ("SILVERJET DGH 55LT-25C") was applied to the heat-shrink film using a cotton tipped swab and allowed to thoroughly dry overnight at room temperature for 16 hours. Next, two 1.3×3.8 cm strips of 200MP lined transfer adhesive were laminated on the same side of the heat-shrink film as the silver ink, 0.5 cm from opposite edges of the film, running parallel to the strips of double coated tape. A razor blade was then used to perforate the film by cutting a series of small slits in a line down the center of the film between the two strips of transfer adhesive. The liner of one of the strips of double coated tape was removed, and the exposed adhesive of the tape was applied to the 5×7.5 cm glass slide. A rubber roller was used to press the adhesive into the glass slide to ensure proper adhesion. The liner of the other strip of double coated tape was removed and the exposed adhesive of the tape applied to the glass slide so that the heat-shrink film was taut. A rubber roller was then used to press the adhesive into the glass slide and ensure proper adhesion.

The liners of the transfer adhesive were removed to expose the adhesive. CER-1 ("AMBERLYST 15H") was added by pouring it over the exposed adhesive. To ensure good adhesion of the sorbent, a piece of weighing paper was placed over the sensor sample, and a rubber roller was used to gently press the sorbent into the adhesive. The glass slide was tipped on its side and lightly tapped to remove any loose sorbent. The sorbent loading was 281 gsm. The sensor was exposed to EO using the procedure described above (see Procedure for Exposing Sensors to Ethylene Oxide). After exposure, the sensor sample (EX-5) was significantly deformed, and the heat-shrink film had torn along the perforation that was made in the sensor sample severing the silver trace of the sensor sample in half.

Example 6 (EX-6): Preparation of Irreversible Temperature Indicator Based Sensor 3M polyester tape 8403 was placed on the front ends of a Telatemp Temperature Recorder label (Style No. 90859, 38-66° C.) to adhere the label face down on a 2×3 inch (5.1 cm×7.6 cm) glass slide taking care to ensure the tape did not cover any of the indicator sections. The liner on the back side of the label was removed to expose the adhesive and allow the sorbent to be bonded to the back of the label. The sorbent was added by pouring it over the exposed adhesive. To ensure good adhesion of the sorbent, a piece of weighing paper was placed over the entire sample and a rubber roller was used to lightly press the sorbent into the adhesive so as to take care to not crush the sorbent particles or break the glass slide. The glass slide was then tipped on its side and lightly tapped to remove any loose sorbent.

A comparative example (CE-1) was prepared by attaching the Teletemp Temperature Recorder label face down on a glass slide with its back liner removed as described above, but no sorbent was adhered to the label.

Each sensor sample (CE-1 and EX-6) was exposed to EO as described in the Procedure for Exposing Sensors to Ethylene Oxide. The sorbent used to prepare each irreversible temperature indicator based sensor sample, the sorbent loading, and the peak temperature indicated on the label for CE-1 and EX-6 after exposure to EO are summarized in Table 4. The peak temperature for CE-1 did not exceed the temperature at which the EO exposure process was performed (55° C.).

TABLE 4

Details of sensor samples CE-1 and EX-6
and their response to EO exposure.

| Example | Sorbent | Sorbent Loading, gsm* | Peak Temperature Indicated, ° C. |
|---------|---------|----------------------|----------------------------------|
| CE-1 | none | 0 | 54 |
| EX-6 | CER-1 | 311 | 66 |

*gsm = grams per square meter

The complete disclosures of the patents, patent documents, and publications cited herein are incorporated by reference in their entirety as if each were individually incorporated. Various modifications and alterations to this disclosure will become apparent to those skilled in the art without departing from the scope and spirit of this disclosure. It should be understood that this disclosure is not intended to be unduly limited by the illustrative embodiments and examples set forth herein and that such examples and embodiments are presented by way of example only with the scope of the disclosure intended to be limited only by the claims set forth herein as follows.

What is claimed is:

1. An ethylene oxide sterilization sensor comprising:
   at least one thermal indicator component independently selected from an electronic thermal sensor, an irreversible temperature indicator, or a heat-shrinkable film;
   an acid-functional porous sorbent or an acid-functional nonwoven fibrous substrate in thermal contact with the at least one thermal indicator component; and
   an acid having a boiling point above 120° C. and a pKa of no greater than 2.5, wherein the acid comprises acid moieties covalently attached to the porous sorbent or to the nonwoven fibrous substrate;
   with the proviso that the sensor comprises at least one of the electronic thermal sensor, the irreversible temperature indicator, or the acid-functional nonwoven fibrous substrate.

2. The sterilization sensor of claim 1, wherein the electronic thermal sensor is present and comprises at least one of a thermocouple, a resistor, a capacitor, an inductor, or an electronic circuit that changes when exposed to a specific minimum elevated temperature.

3. The sterilization sensor of claim 2, wherein the electronic thermal sensor comprises an RFID tag.

4. The sterilization sensor of claim 1, which detects ethylene oxide at a concentration of 3,000 parts per million (ppm) or greater in a gas.

5. The sterilization sensor of claim 1, wherein the heat-shrinkable film is present.

6. The sterilization sensor of claim 1, wherein the irreversible temperature indicator is present and comprises a thermochromic dye.

7. The sterilization sensor of claim 1, wherein the acid-functional porous sorbent is present and comprises activated carbon, porous silica, zeolites, porous organic polymer, or combinations thereof.

8. The sterilization sensor of claim 7, wherein the acid comprises acid compounds impregnated within the porous sorbent.

9. The sterilization sensor of claim 8, wherein the acid compounds comprise sulfuric acid, phosphoric acid, methanesulfonic acid, methanephosphonic acid, benzene sulfonic acid, toluene sulfonic acid, or a combination thereof.

10. The sterilization sensor of claim 1, wherein the acid-functional porous sorbent is present in an amount of 10 grams per square meter (gsm) to 1000 gsm of an area of the ethylene oxide sterilization sensor.

11. The sterilization sensor of claim 1, wherein the acid-functional nonwoven fibrous substrate is present and comprises a plurality of fibers comprising polypropylene, polyethylene terephthalate (PET), polylactic acid (PLA), polyphenylene sulfide (PPS), or any combination thereof.

12. The sterilization sensor of claim 1, wherein the acid comprises the acid moieties covalently attached to the nonwoven fibrous substrate.

13. The sterilization sensor of claim 12, wherein the covalently attached acid moieties are selected from sulfonic acid ($-SO_3H$) groups or phosphonic acid ($-PO_3H_2$) groups.

14. The sterilization sensor of claim 12, wherein the acid is present in an amount of 0.2 mmole to 5.5 mmole of the acid moieties per gram of the acid-functional porous sorbent or 1 mmole to 3 mmole of the acid moieties per gram of the acid-functional nonwoven fibrous substrate.

15. The sterilization sensor of claim 1, wherein the acid-functional porous sorbent or the acid-functional nonwoven fibrous substrate is adhered to the at least one thermal indicator component.

16. The sterilization sensor of claim 1, wherein the acid-functional porous sorbent is present in the form of particles.

17. An array comprising a plurality of the ethylene oxide sterilization sensors of claim 1.

18. A method of detecting ethylene oxide in a sterilization process, the method comprising:

proviso the ethylene oxide sterilization sensor of claim 1;

allowing the ethylene oxide to contact the acid to generate thermal energy sufficient to cause a response from the at least one thermal indicator component; and detecting that conditions for the sterilization process have been met.

19. The method of detecting of claim 18, wherein the detecting comprises exposing an underlying image.

\* \* \* \* \*